US012569430B2

(12) United States Patent
Granier et al.

(10) Patent No.: US 12,569,430 B2
(45) Date of Patent: Mar. 10, 2026

(54) BIODEGRADABLE IMPLANT INCLUDING NALTREXONE

(71) Applicant: BioCorRx, Inc., Anaheim, CA (US)

(72) Inventors: Brady J. Granier, Sherman Oaks, CA (US); Ashok Kumar, Northants (GB); Vitalii E Stelmakh, Mechanicsville, VA (US); Robert P Giannini, Jr., Riverside, CA (US); Andrew Peter Mallon, Lincoln, RI (US); George Edward Sherman, Jr., Pine Knoll Shores, NC (US)

(*) Notice: Subject to any disclaimer, the term of this patent is extended or adjusted under 35 U.S.C. 154(b) by 46 days.

(21) Appl. No.: 17/711,910

(22) Filed: Apr. 1, 2022

(65) Prior Publication Data

US 2023/0097377 A1     Mar. 30, 2023

Related U.S. Application Data

(60) Provisional application No. 63/245,563, filed on Sep. 17, 2021.

(51) Int. Cl.
| | |
|---|---|
| *A61K 9/00* | (2006.01) |
| *A61J 3/02* | (2006.01) |
| *A61K 9/16* | (2006.01) |
| *A61K 31/485* | (2006.01) |
| *A61P 25/18* | (2006.01) |
| *A61P 25/32* | (2006.01) |
| *A61P 25/36* | (2006.01) |

(52) U.S. Cl.
CPC .............. *A61K 9/0024* (2013.01); *A61J 3/02* (2013.01); *A61K 9/1617* (2013.01); *A61K 9/1688* (2013.01); *A61K 31/485* (2013.01); *A61P 25/18* (2018.01); *A61P 25/32* (2018.01); *A61P 25/36* (2018.01)

(58) Field of Classification Search
None
See application file for complete search history.

(56) References Cited

U.S. PATENT DOCUMENTS

| | | | |
|---|---|---|---|
| 4,452,775 | A | 6/1984 | Kent |
| 4,748,024 | A | 5/1988 | Leonard |
| 6,203,813 | B1 * | 3/2001 | Gooberman ........... A61K 45/06 |
| | | | 514/812 |
| 7,858,110 | B2 | 12/2010 | Kuzma et al. |
| 7,914,804 | B2 | 3/2011 | O'Neil et al. |
| 7,919,499 | B2 | 4/2011 | Ehrich |
| 8,460,274 | B2 | 6/2013 | Kuzma et al. |
| 8,784,865 | B2 | 7/2014 | Kuzma et al. |
| 9,283,212 | B2 | 3/2016 | O'Neil |
| 10,507,184 | B2 | 12/2019 | Sexena et al. |
| 11,197,819 | B1 | 12/2021 | Benner et al. |
| 2003/0007992 | A1 * | 1/2003 | Gibson ................ A61K 9/0024 |
| | | | 424/425 |
| 2007/0065364 | A1 * | 3/2007 | Oshlack ............... A61K 9/1694 |
| | | | 424/10.1 |
| 2011/0287101 | A1 | 11/2011 | Guarnieri |
| 2019/0099364 | A1 * | 4/2019 | Felix ......................... A61P 3/04 |
| 2019/0307691 | A1 | 10/2019 | Gaillard et al. |
| 2020/0289408 | A1 | 9/2020 | Mallon |
| 2021/0015742 | A1 | 1/2021 | Felix et al. |
| 2021/0244818 | A1 | 8/2021 | Ehrich |
| 2021/0393516 | A1 | 12/2021 | Mallon |
| 2022/0062277 | A1 | 3/2022 | Lin et al. |

FOREIGN PATENT DOCUMENTS

| | | | |
|---|---|---|---|
| EP | 0 862 416 | 5/1997 | |
| JP | 2007/254433 A | 10/2007 | |
| RU | 2620254 C1 | 5/2017 | |
| WO | WO-9830171 A1 * | 7/1998 | ........... A61K 31/439 |
| WO | WO2017/033208 A2 | 3/2017 | |
| WO | WO2018/191430 A1 | 10/2018 | |
| WO | WO2022/147236 A1 | 7/2022 | |

OTHER PUBLICATIONS

Bremner JD et al., (1991), "Animal Models for the Neurobiology of Trauma," PTSD Res Quart, 2(4):1-8.
Brush FB (2003), "Selection for Differences in Avoidance Learning: The Syracuse Strains Differ in Anxiety, Not Learning Ability," Behav Genet, 33(6)677-96.
Jenab S et al., (1995), Assessment of delta Opioid Antinociception and Receptor mRNA Levels in Mouse After Chronic Naltrexone Treatment, Brain Res, 691(1-2):69-75.
Krupitsky E et al.,(2012), "Randomized Trial of Long-Acting Sustained-Release Naltrexone Implant vs Oral Naltrexone . . . ," Arch Gen Psych, 69(9):973-81.
Misra AL and Pontani RB, (1981), "An Improved Long-Acting Delivery System for Narcotic Antagonists," NIDA Res Monogr, 28:254-64 (Abstract Only).
Olsen JL, (1981), "Solid Solutions as Long-Acting Naltrexone Delivery Systems," NIDA Res Monogr, 28:265-71 (Abstract Only).
Piper J (Manager), (2020), "Patentability Search: Naltrexone Implantable Pellet Composition," Cardinal Intellectual Property, Evanston, IL (8 pages).
Rothman RB et al., (1989), "Chronic Administration of Morphine and Naltrexone Up-Regulate u-Opioid Binding Sites . . . ," Eur J Pharmacol, 160(1):71-82.
HITT EP, (2008), "FDA Warns About Injection Site Reactions with Naltrexone," Medscape, downloaded from the internet at www.medscape.com on Aug. 21, 2025, (1 page).
Jane Darwin v. Lance L. Gooberman, M.D., et al., Docket No. A-1997-99T3, Mar. 5, 2001, Appellate Division, Superior Court of New Jersey.

* cited by examiner

*Primary Examiner* — Robert A Wax
*Assistant Examiner* — William Craigo
(74) *Attorney, Agent, or Firm* — Feeney IP Law; Alan F Feeney; Logan D Faucher

(57) ABSTRACT

A formulation of naltrexone that ameliorates undesirable localized reactions at the site of implantation.

3 Claims, 5 Drawing Sheets

BIODEGRADABLE IMPLANT INCLUDING NALTREXONE

CROSS-REFERENCE TO RELATED APPLICATIONS

This application claims priority to U.S. Provisional Application No. 63/245,563 filed on Sep. 17, 2021. The entire contents are incorporated herein by reference.

BACKGROUND OF THE INVENTION

Naltrexone is a prescription drug belonging to a class of drugs called opioid antagonists. Naltrexone, however, may cause undesirable localized reactions at the site of implantation. Applicant has developed a formulation of naltrexone that ameliorates or otherwise eliminates such reactions, various solutions to which are described with respect to several embodiments described herein.

BRIEF SUMMARY OF THE INVENTION

In one aspect, the disclosure provides a subcutaneous biodegradable medical implant comprising relatively pure naltrexone, wherein the subcutaneous biodegradable medical implant is capable of releasing a dosage amount of the naltrexone from the subcutaneous biodegradable medical implant following subcutaneous placement of the subcutaneous biodegradable medical implant in vivo without causing undesirable reactions at the implantation site observed when prior art naltrexone implants are used. The subcutaneous biodegradable medical implant is useful in preventing and treating diseases and disorders in a patient, including addictive disorders (e.g., including opioid use disorder, alcohol use disorder, opioid addiction, alcohol addiction, addictive personality disorders, gaming or gambling addictions, social media addiction, screen addiction, and the like), obesity, and weight gain.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Figure 1:
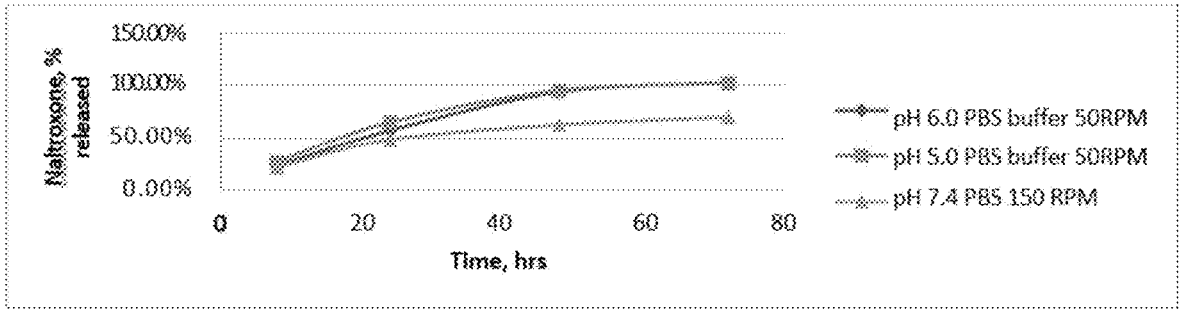

Having thus described the disclosure in general terms, reference will now be made to the accompanying drawings, which are not necessarily drawn to scale, and wherein:

FIG. 1 is a graph plotting the release of naltrexone from BICX in 10 μM phosphate buffer at different pHs over 72 hours.

Figure 2:
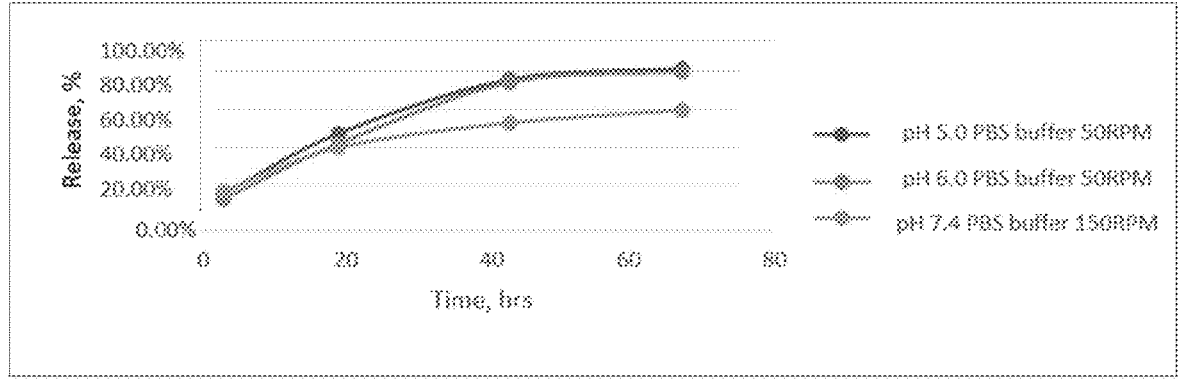

FIG. 2 is a graph plotting the release of triamcinolone acetonide (TCA) from BICX in 10 μM phosphate buffer at different pHs over 72 hours.

Figure 3:
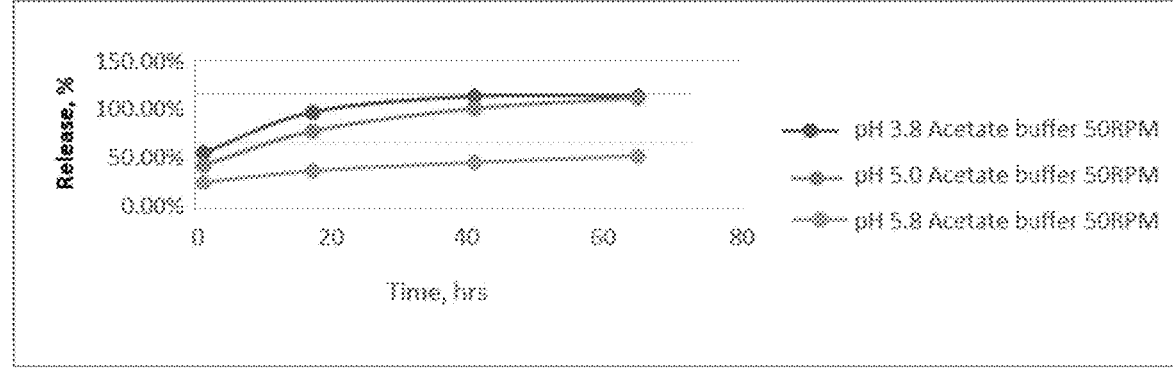

FIG. 3 is a graph plotting the release of naltrexone from BICX in 10 μM phosphate buffer at different pHs over 72 hours.

Figure 4:
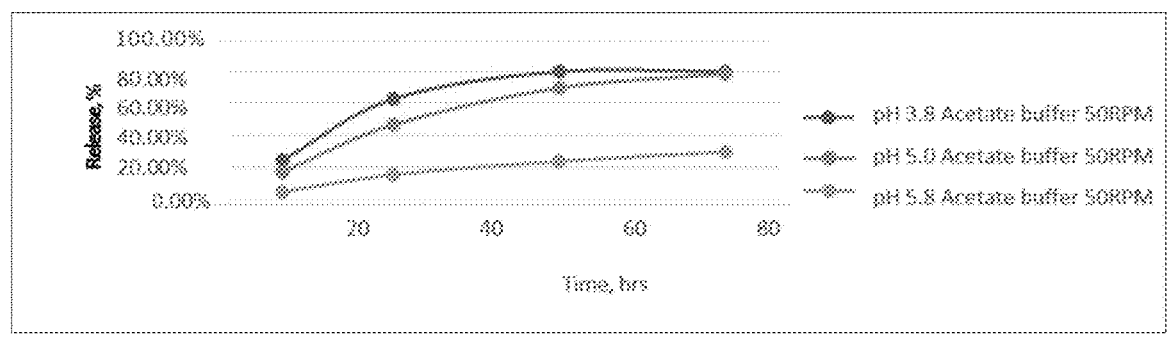

FIG. 4 is a graph plotting the release of triamcinolone acetonide (TCA) from BICX in 10 μM phosphate buffer at different pHs over 72 hours.

Figure 5:
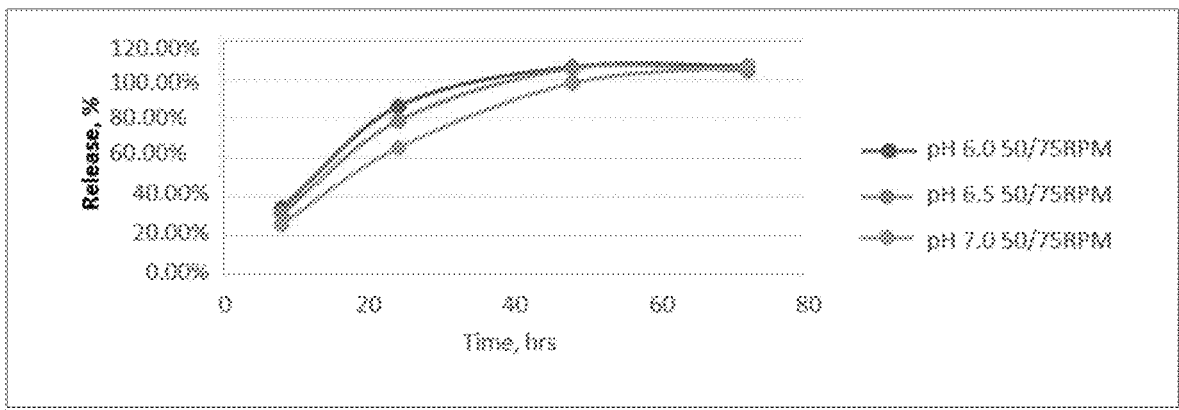

FIG. 5 is a graph plotting the release of naltrexone from BICX in 10 μM phosphate buffer/20% EtOH at different pHs over 72 hours.

Figure 6:
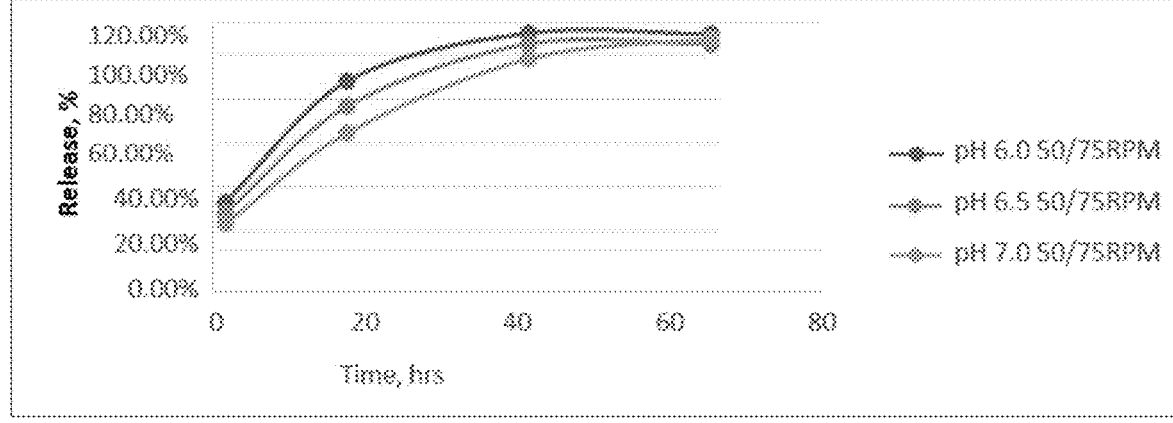

FIG. 6 is a graph plotting the release of triamcinolone acetonide (TCA) from BICX in 10 μM phosphate buffer/20% EtOH at different pHs over 72 hours.

Figure 7:
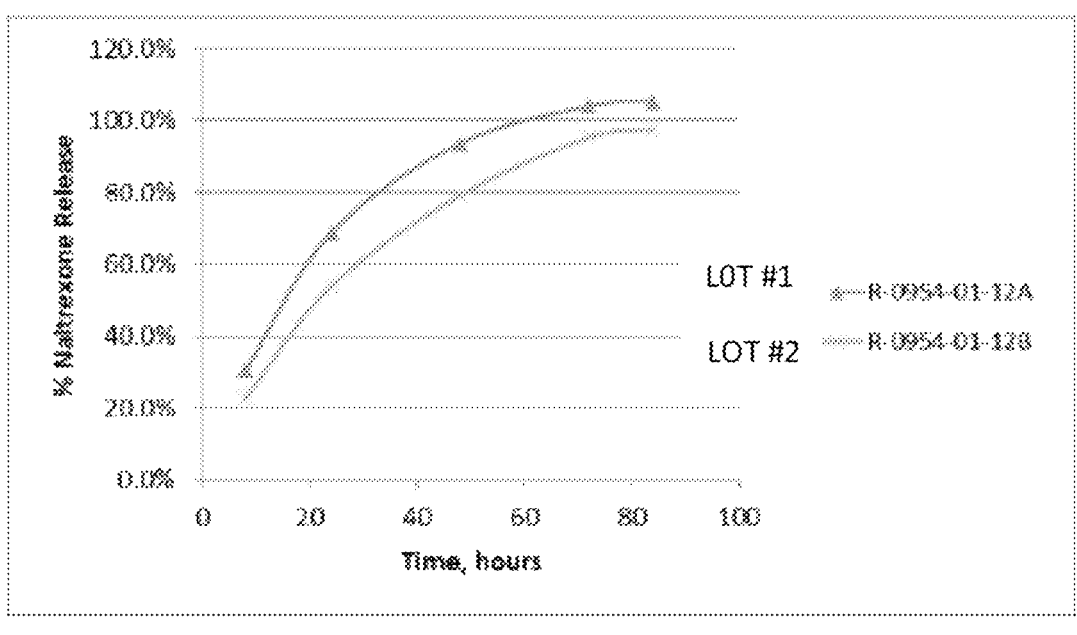

FIG. 7 is a graph plotting the release of naltrexone from BICX in 10 μM phosphate buffer/20% EtOH over 72 hours.

Figure 8:
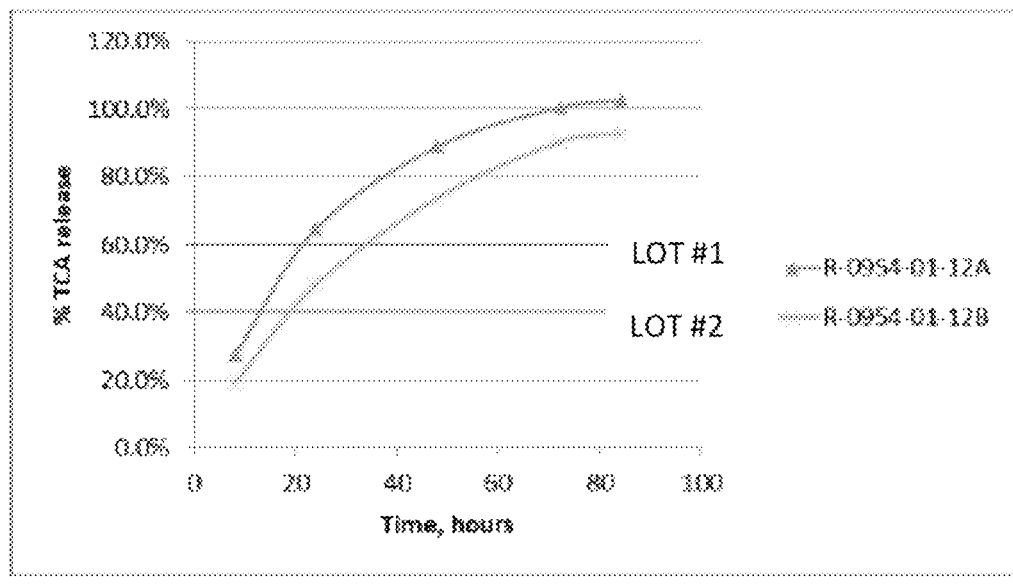

FIG. 8 is a graph plotting the release of triamcinolone acetonide (TCA) from BICX in 10 μM phosphate buffer/20% EtOH over 84 hours.

Figure 9:
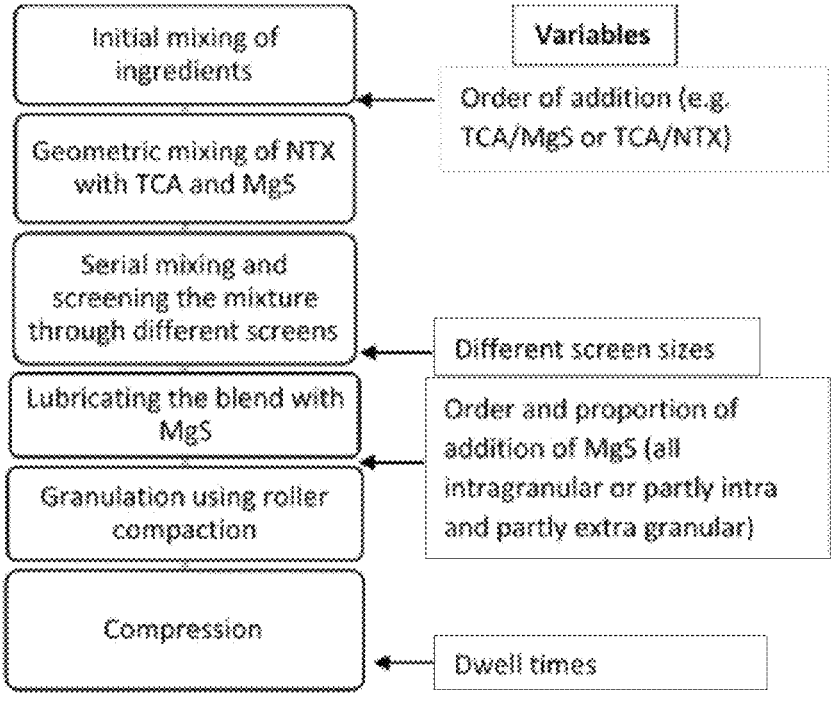

FIG. 9 is a process flow chart detailing the variables tested in the order of testing during the development of BICX over 84 hours.

Figure 10:
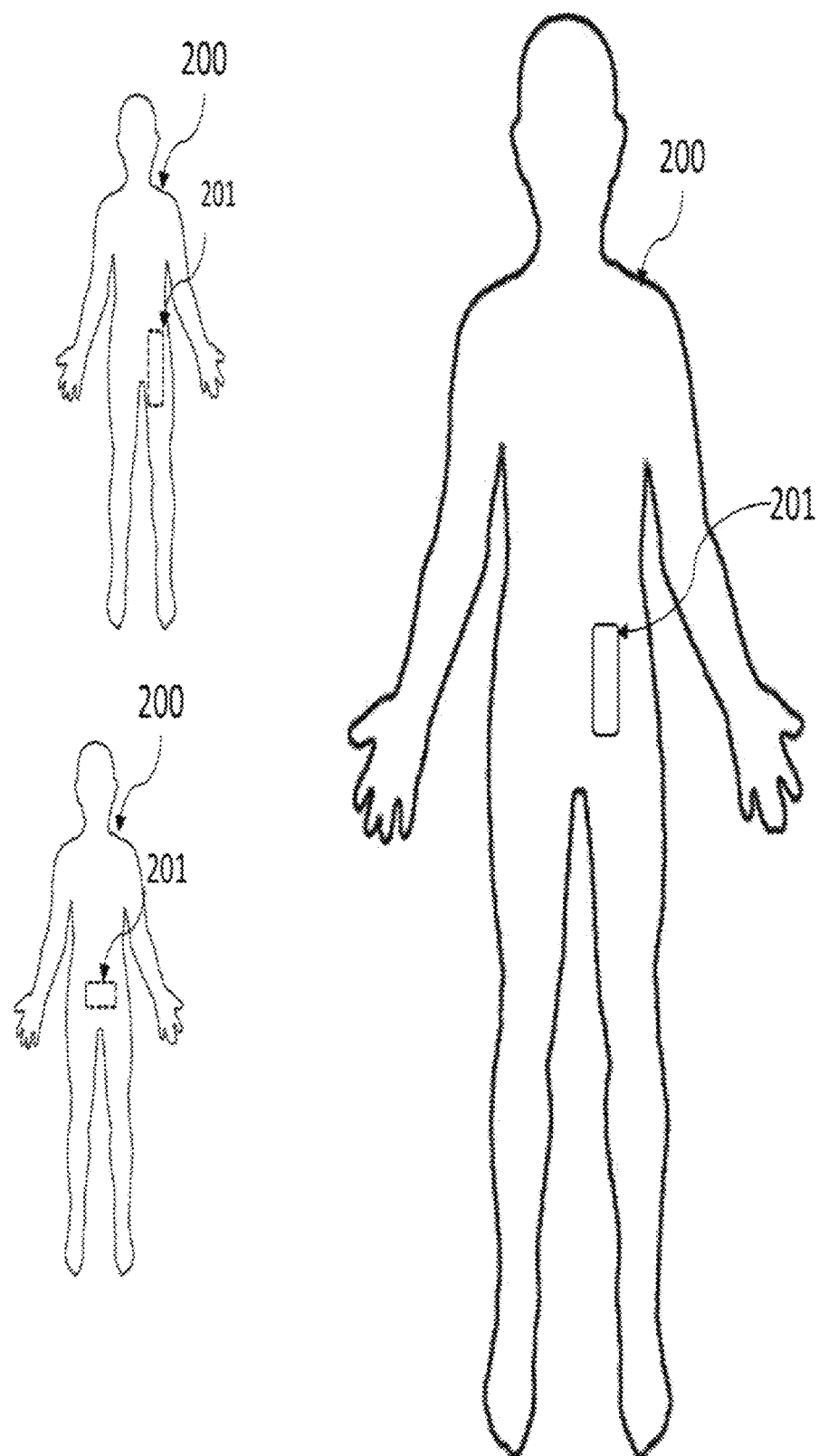

FIG. 10 is a diagram of an exemplary subcutaneous implant placed in a patient according to embodiments of the present disclosure.

DETAILED DESCRIPTION OF VARIOUS EMBODIMENTS

Various embodiments of the present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Within the framework of the present description and in the subsequent claims, except where otherwise indicated, all numbers expressing amounts, quantities, percentages, and so forth, are to be understood as being preceded in all instances by the term "about". As used herein, the term "about" is defined as ±5%. Also, all ranges of numerical entities include all the possible combinations of the maximum and minimum numerical values and all the possible intermediate ranges therein, in addition to those specifically indicated hereafter. The term "and/or" as used herein is defined as the possibility of having one or the other or both. For example, "A and/or B" provides for the scenarios of having just A or just B or a combination of A and B. If the claim reads A and/or B and/or C, the composition may include A alone, B alone, C alone, A and B but not C, B and C but not A, A and C but not B or all three A, B and C as components.

Definitions

The term "biodegradable," as used herein, refers, in one embodiment, to a material that is degraded in a biological environment. In another embodiment, "biodegradable" refers to a material that has a finite half-life in a biological environment. In another embodiment, "biodegradable" refers to a material that has a measurable half-life in a biological environment. In another embodiment, "biodegradable" refers to a material that is degraded inside a living organism. In another embodiment, "biodegradable" refers to a material that has a finite half-life inside a living organism. In another embodiment, "biodegradable" refers to a material that has a measurable half-life inside a living organism.

The terms "implant" or "implants," as used herein, refers to something implanted into a tissue of a human, in particular pharmaceutically-acceptable, i.e., that which is useful in preparing a pharmaceutical composition that is generally safe, non-toxic and neither biologically nor otherwise undesirable and includes that which is acceptable for veterinary use as well as human pharmaceutical use, controlled/sustained drug delivery systems. The terms also refer to implantable pellet(s). The term "formulation," more precisely a "pharmaceutical formulation," as used herein, refers to, in pharmaceutics, is the combination of different chemical substances, including the active drug, in a final medicinal product.

The term "NOAEL," as used herein, refers to "no observed adverse event level."

The term "relatively pure" refers to an implant comprised of 95%, preferably 97.5% or more naltrexone.

In one embodiment, the half-life is 1 month or less. In another embodiment, the half-life is 2 months or less. In another embodiment, the half-life is 3 months or less. In another embodiment, the half-life is 4 months or less. In another embodiment, the half-life is 5 months or less. In another embodiment, the half-life is 6 months or less. In another embodiment, the half-life is 8 months or less. In another embodiment, the half-life is 10 months or less. In another embodiment, the half-life is one year or less. In another embodiment, the half-life is 1.5 years or less. In another embodiment, the half-life is 2 years or less. In another embodiment, the half-life is 3 years or less. In another embodiment, the half-life is 4 years or less. In another embodiment, the half-life is 5 years or less. In another embodiment, the half-life is 7 years or less. In another embodiment, the half-life is 10 years or less. Each possibility represents a separate embodiment of the present disclosure.

Compositions or methods "comprising" or "including" one or more recited elements may include other elements not specifically recited.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

The singular forms of the articles "a," "an," and "the" include plural references unless the context clearly dictates otherwise.

A. Overview

Various embodiments of the disclosure generally relate to a subcutaneous biodegradable medical implant comprising relatively pure naltrexone (e.g., naltrexone hydrochloride, naltrexone base, naltrexone anhydrous base) that, when implanted in a patient, aids in treatment of diseases and disorders in the patient. In some embodiments, the medical implant further comprises less than 10% cholesterol, preferably about 2%, in the blend and/or as an outer coating. Implants of the disclosure are useful in treating an addiction disorder, including but not limited to opioid use disorder, opioid addition, alcohol use disorder, use of illicit drugs such as, but not limited to, cocaine, methamphetamine and cannabis gambling addiction, gaming addiction, sex addiction, screen addiction, social media addiction, or obsessive-compulsive disorder, particularly in situations when current treatments abate or become ineffective and the cravings or desires return in the treated patient. Implants of the disclosure are useful in treating obesity, weight gain, and weight gain associated with hypothyroidism, Hashimoto's thyroiditis, polycystic ovary syndrome (PCOS), or sleep apnea.

Implants of the disclosure are useful in treating chronic pain, inflammation, and complex regional pain syndrome in the patient.

The molecular formula for naltrexone is (4R,4aS,7aR,12bS)-3-(cyclopropylmethyl)-4a,9-dihydroxy-2,4,5,6,7a,13-hexahydro-1H-4,12-methanobenzofuro[3,2-e]isoquinolin-7-one ($C_{20}H_{23}NO_4$). It will be appreciated that naltrexone may also be referred to as Vivitrex, ReVia, N-cyclopropylmethylnoroxymorphone, Vivitrol®, Celupan, Naltrexonum, Trexan, Naltrexona, Naltrel, N-Cyclopropyl-methyl-14-hydroxidihydromorphinone, among others. The present application applies to the use of the identified molecular formula, regardless of what terminology is used to reference it.

It will be appreciated that the biodegradable embodiments of the present disclosure eliminate a need for physical or intentional removal of the implants from a patient. The implant comprising naltrexone may biodegrade into the bloodstream, eliminating the requirement for removal of the implant, over a varying number of days or months depending on the metabolism of the patient. The implant comprising naltrexone provides a sustained release of naltrexone into the bloodstream of the patient. The implant comprising naltrexone provides a gradually descending sustained level of release of naltrexone into the bloodstream of the patient over the course of treatment. Such sustained release of naltrexone into the bloodstream overcomes several drawbacks associated with oral-based medication administration systems.

The present implants comprising naltrexone eliminate the need for oral administration, which eliminates the need for a patient's liver to process the drug. Such a bypass is significantly beneficial for those patients with fatty liver disease and other conditions that would prohibit a patient from processing naltrexone in a healthy manner. An implant opens the door for patients who may not otherwise be candidates for treatments involving administration of naltrexone. Additionally, oral administration tends to require a higher dosage than is required when using an implant.

Further, in an oral-based naltrexone administration system, non-compliance with the medication plan is a common issue. Reasons for non-compliance include a patient forgetting to take the medication at the scheduled time (e.g., forgetting to take the medication every day; forgetting to take the medication at the same time each day) and a patient opting not to take the medication as a result of distaste for or discomfort related to possible side effects, for example gastrointestinal complaints, including but not limited to, diarrhea and abdominal cramping, liver damage, and more. Examples of side effects associated with oral administration of naltrexone may include symptoms of anxiety, allergic dermatitis, arthralgias, myalgias, insomnia, fatigue, skin rash, headache disorder, nausea, vomiting, abdominal pain with cramps, angioedema, among others. Such non-compliance significantly reduces likelihood of long-term success of a treatment regimen.

Patients receiving administration of naltrexone sometimes preferably meet certain physical requirements in order for the implant to be safe and successful. Examples of such physical requirements vary according to the intended treatment or indication, and may include without limitation specific liver enzyme levels, certain BMI levels, and the patient should not be taking any opioids.

Adverse reactions at the implantation site have been reported (Krupitsky E et al. (2012), Arch Gen Psychiatry, 69(9):973-81). These reactions include, but are not limited to, swelling, redness, pain and itching. Applicant has discovered that an ingredient found in many naltrexone formulations (See, U.S. Pat. No. 6,203,813 (Gooberman, 2001)), triamcinolone acetonide (TCA), believed to prevent adverse tissue reactions, is actually the cause of such adverse tissue reactions. In addition, Applicant has found that a common carrier used in prior art formulations, magnesium stearate, when used in excess amounts, can also contribute to the adverse tissue reactions observed in many patients receiving such implants. Russian Patent No. 2620254 (Saksena K et al., 2017) teaches "that magnesium salts or magnesium stearate in combination with naltrexone in implantable tablets cause irritation and inflammation at the site of implantation." Applicant found, however, that magnesium stearate in amounts less than 1.5%, preferably less than 1.2%, more preferably about 1.08%, of the total mass of formulation is the minimum amount of magnesium stearate required to prevent "sticking" during the formation of the implant while not causing adverse reactions at the implant site. "Sticking" during the manufacturing process results in uneven and/or inconsistent implants and the inability to use a fully automated, hydraulic pellet press to produce uniform and/or consistent implants Applicant, however, discovered that use of magnesium stearate in amounts greater than 1.2% of the formulation resulted in the site implantation irritation as reported in the art (Ibid, Krupitsky E et al.) Finally, Applicant discovered that use of poly-lactic acid-based polymer matrixes, such as poly(lactic-co-glycolic acid), ("PLGA") to coat an inner naltrexone core as described in Russian Patent No. 2620254 (Ibid, Saksena K et al.) and U.S. Pat. No. 7,914,802 (O'Neil, 2016) was undesirable as such polymers take longer to be bio-absorbed than the naltrexone core giving false impressions that the implant still contains naltrexone. In addition, un-absorbed poly-lactic acid based polymer matrixes can result in the undesirable appearance of lumps. Applicant has developed a formulation that does not include triamcinolone acetonide (TCA) and poly-lactic acid-based polymer matrixes, and includes only trace amounts of magnesium stearate, to minimize, reduce or eliminate adverse site reactions found in the prior art implants while providing enough magnesium stearate to prevent sticking and allow for adequate compression using a commercially automated pellet press. The present invention is directed to implants containing 97.5% or more naltrexone that are capable of being manufactured on semi- or fully-automatic pellet press due to the inclusion of a small percentage of magnesium stearate. The preferred embodiment does not contain triamcinolone acetonide (TCA).

B. Composition of Naltrexone Pellets and Process to Manufacture

In some embodiments, the subcutaneous biodegradable medical implant may comprise other excipients and/or non-active ingredients as part of the manufacturing process. Exemplary excipients and/or non-active ingredients may include cholesterol.

One embodiment of the present invention is directed to a robust process to produce reproducible implantable pellets containing naltrexone (NTX) at scale. To confirm the dissolution rate in vitro and release rate of the naltrexone in vivo in a pig model of the pellets, placebo pellets were manufactured. The pellets were manufactured and tested by IRISYS, Inc., San Diego, California (US).

The composition of the placebo and the naltrexone-based pellets are provided in Tables 1a-1c.

TABLE 1a

Composition of placebo Naltrexone pellet (implant)

| Item # | Ingredient | Amount per Implant (mg) | Function |
|---|---|---|---|
| 1 | Spray Dried Lactose, Flowlac ® 90 (MEGGLE Group GmbH, Wasserburg, DE) | 800 | Filler |
| 2 | Cholesterol, Ultra-pure grade | 200 | For extended release of TCA |
| 3 | Triamcinolone acetonide (TCA) Sterile Micronized (TCA) | 10 | Reduces pain and local tissue inflammation at the implantation site during use and may extend the release profile in vivo |
| 4 | Magnesium Stearate, Hyqual ® (Mallinckrodt, Inc., St. Louis, MO), Vegetable Source, NF— GenAR ® (Mallinckrodt, Inc., St. Louis, MO), | 11 | Lubricant |
| | Total Quantity Weighed | 1021 | |

TABLE 1b

Composition of Naltrexone alone pellet (implant)

| Item # | Ingredient | Amount per Implant (mg) | Function |
|---|---|---|---|
| 1 | Naltrexone | 1000 | Opioid antagonist |
| 3 | Magnesium Stearate, Hyqual ® (Mallinckrodt, Inc., St. Louis, MO), Vegetable Source, NF— GenAR ®, (Mallinckrodt, Inc., St. Louis, MO) | 11 | Lubricant |
| | Total Quantity Weighed | 1011 | |

TABLE 1c

Composition of combination Naltrexone/triamcinolone acetonide (TCA) pellet (implant)

| Item # | Ingredient | Amount per Implant (mg) | Function |
|---|---|---|---|
| 1 | Naltrexone | 1000 | Opioid antagonist |
| 2 | Triamcinolone acetonide (TCA) Sterile Micronized | 10 | Reduces pain and local tissue inflammation at the implantation site during use and may extend the release profile in vivo e |
| 3 | Magnesium Stearate, Hyqual ® (Mallinckrodt, Inc., St. Louis, MO), Vegetable Source, NF— GenAR ® (Mallinckrodt, Inc., St. Louis, MO), | 11 | Lubricant |
| | Total Quantity Weighed | 1021 | |

B1. Materials and Equipment

Details of the materials used are listed in Tables 2a-2b.

TABLE 2A

| List of materials | | |
|---|---|---|
| Material | Manufacturer | Lot# |
| Naltrexone base | Noramco ®, Inc., Wilmington, DE, US | 6064730, 6066328 |
| Triamcinolone acetonide (TCA) | Farmabios ®, S.p.A., Grapello Cairoli, IT | 2196SM20011723, 2196SM20121823 |
| Magnesium Stearate | Macron Fine Chemicals ®, Avantor ® Performance Materials, Inc., Center Valley, PA | A114302L01 |

TABLE 2B

| List of equipment |
|---|
| V-blender BL-001 (Munson ® Machinery Co., Inc., Utica, NY) |
| Natoli ® NP20A model pellet press (Natoli ® Engineering Co., Inc., St. Charles, MO) |
| Screens: 18, 30, 40, 80, 140, 200 mesh |
| Roller compactor equipped with 20 and 40 mesh screens. |

B2. Manufacturing Process Development

The process involved material de-lumping, triamcinolone acetonide (TCA) and magnesium stearate blending with naltrexone, pellet compression, packaging, and gamma-sterilization. The first blend was prepared based on the provided procedure. In one embodiment, 100 g of naltrexone (NTX) sample, 1 g of TCA sample and 1.1 g of magnesium stearate sample were passed through 18-mesh screen and blended into a plastic bag. Other embodiments did not contain TCA, only naltrexone and 1.1 g of magnesium stearate. The resulting blend was passed through an 18-mesh screen three (3) times to de-lump and to ensure uniformity. Pellets were compressed on a Natoli® NP20A single punch hydraulic pellet press (Natoli® Engineering Company, Inc., Saint Charles, MO) using an 8.4 mm round flat face tooling. The pellet press was run in manual mode and the die was filled with a pre-weighed amount of the blend (1.021 g). The press did not have a double fill/pre-compression option in manual mode, so the blend was manually pre-compressed between two plastic sheets to simulate dry granulation or roller compaction and then the die was filled with the blend. An 8.4 mm round flat face tooling (Table 3) was used during the compressing step.

TABLE 3

| Compression of blend R-0954-01 to produce pellet R-0954-01-03 and R-0954-01-05. | | | |
|---|---|---|---|
| Pellet blend number | Thickness set point, mm | Compression pressure, kN | Pellet description |
| R-0954-01-03/05 | 17.25 | 4-5 | round 8.4 mm pellet; hardness ~17 kg (old tester) |

Finished pellet length was 17.5±0.25 mm and actual compression pressure was 3.5±0.7 kN.

B3. Dissolution Method Development

Acceptable pellets from the blend were used for in vitro dissolution method development; an important tool used for development and approval of generic dosage forms. The pellets were tested using different media at different pHs as shown in Table 5 in Stage 1 of dissolution method development. The parameters used in the dissolution study are given below.

B3.1 Stage 1. Dissolution Method Parameters Determined

A USP dissolution apparatus II (paddle) (Agilent Technologies, Inc., Santa Clara, CA) was used for dissolution method parameters selection. For accelerated dissolution method development multiple parameters were evaluated:

1). temperature of the dissolution media;

2). initial wetting of the pellet (by adding detergent and organic solvent);

3). the mixing speed; and

4). the pH of the dissolution media used.

Water was used as the starting media. A sampling time-point (at 66 or 90 hours) was used for initial dissolution parameter assessment.

TABLE 4

| Results of the initial assessment of influence of different dissolution parameters (n = 1) | | | | | | | | |
|---|---|---|---|---|---|---|---|---|
| Dissolution Media | | Water | | 20% EtOH, 80% Water | 0.1% SLS in Water | 0.05N HCl | 10 mM PBS pH 7.4 | 20 mM Acetate Buffer pH 3.8 |
| pH | — | — | — | — | — | 1 | 7.4 | 3.8 |
| RPM | 50 | 60 | 150 | 50 | 50 | 50 | 50 | 50 |
| Temperature | 37° C. | 60° C. | 37° C. | 37° C. | 37° C. | 37° C. | 37° C. | 37° C. |
| Time | 90 hrs | 66 hrs | 66 hrs | 90 hrs | 66 hrs | 66 hrs | 66 hrs | 66 hrs |
| Release Naltrexone recovery % | 36.05 | 43.76 | 36.67 | 60.52 | 38.21 | 99.19 | 42.51 | 99.79 |
| Release Triamcinolone, % | 31.50 | 38.63 | 33.47 | 61.77 | 39.09 | 85.59 | 33.12 | 83.52 |

The following was observed:

1. a higher temperature increased dissolution rate of the naltrexone slightly;

2. a lower pH increased the dissolution rate of the naltrexone;

3. the addition of 20% ethanol (EtOH) in water almost doubled the dissolution rate of the naltrexone compared to water alone, however, 100% of release was not achieved over 90 hours. It is expected that increasing the percentage of EtOH will not positively impact dissolution rate since solubility of naltrexone hydrochloride in EtOH is low (<1 mg/mL) and doubling of the dissolution rate is explained with EtOH helping to "wet" the pellet;

4. the addition of 0.1% SLS did not significantly improve dissolution rate;

5. 100% dissolution of naltrexone was achieved over 66 hrs in a 0.05N HCl and 20 mM acetate buffer of pH 3.8; and 6. a phosphate buffered saline (PBS) buffer of a pH 7.4 provided higher dissolution rate than water.

B3.2 Stage 2. Dissolution Method and Parameters Optimization

As 100% dissolution was achieved at pH 1 and pH 3.8, and pH 7.4 provided only 42.51% dissolution as per the data from Stage 1 dissolution method development, for Stage 2 of development two types of physiologically relevant buffers were screened: phosphate buffer and acetate buffers at 10 mM concentration in a range of pH 3.8 to 7.4 with more rigorous sampling. The results are shown in Tables 5 through 8 and FIGS. 1-4.

TABLE 5

Release of naltrexone from pellets in 10 mM phosphate buffer at different pHs (n = 1)

| Time, hrs | 10 mM phosphate buffer pH 5.0 50 RPM at 37° C. | 10 mM phosphate buffer pH 6.0 50 RPM at 37° C. | 10 mM phosphate buffer pH 7.4 150 RPM at 37° C. |
|---|---|---|---|
| 8 | 27.29% | 23.24% | 22.20% |
| 24 | 65.07% | 57.19% | 48.55% |
| 48 | 95.09% | 93.71% | 62.56% |
| 72 | 102.01% | 102.64% | 69.80% |

TABLE 6

Release of triamcinolone acetonide (TCA) from pellets in 10 μM phosphate buffer at different pH (n = 1)

| Time, hrs | 10 mM phosphate buffer pH 5.0 50 RPM at 37° C. | 10 mM phosphate buffer pH 6.0 50 RPM at 37° C. | 10 mM phosphate buffer pH 7.4 150 RPM at 37° C. |
|---|---|---|---|
| 8 | 15.30% | 12.51% | 16.66% |
| 24 | 47.19% | 41.72% | 39.78% |
| 48 | 75.78% | 74.31% | 52.83% |
| 72 | 81.56% | 80.00% | 59.58% |

TABLE 7

Release of naltrexone from pellets in 10 mM acetate buffer at different pH (n = 1)

| Time, hrs | 10 mM Acetate buffer pH 3.8 50 RPM at 37° C. | 10 mM Acetate buffer pH 5.0 50 RPM at 37° C. | 10 mM Acetate buffer pH 5.8 50 RPM at 37° C. |
|---|---|---|---|
| 8 | 39.67% | 26.77% | 9.20% |
| 24 | 81.50% | 62.10% | 21.16% |
| 48 | 97.80% | 85.24% | 29.99% |
| 72 | 97.80% | 96.09% | 36.30% |

TABLE 8

Release of triamcinolone acetonide (TCA) from pellets in 10 μM acetate buffer at different pH (n = 1)

| Time, hrs | 10 mM Acetate buffer pH 3.8 50 RPM at 37° C. | 10 mM Acetate buffer pH 5.0 50 RPM at 37° C. | 10 mM Acetate buffer pH 5.8 50 RPM at |
|---|---|---|---|
| 8 | 24.63% | 17.27% | 4.93% |
| 24 | 62.64% | 46.65% | 15.62% |
| 48 | 79.58% | 69.50% | 23.89% |
| 72 | 79.36% | 78.13% | 29.78% |

As evidenced in FIGS. 1 and 3, the dissolution of naltrexone is pH-dependent and a desirable dissolution profile is achieved by modifying the pH of the dissolution media. As observed in the Stage 1 dissolution method, a lower pH yielded a higher dissolution of naltrexone. A similar trend was observed in both the phosphate and acetate buffers. The dissolution profile was comparable in 10 mM at pH 5.0 phosphate buffer to the same pH 10 mM acetate buffer. Since the phosphate buffer was more physiologically relevant; it was therefore, selected for future experiments. Medias with a pH of 5.0 or lower, dispersed the pellet after 72 hours and none of the conditions provided a 100% release of triamcinolone acetonide (TCA) due to its lipophilic nature. As we 100% TCA release was not achieved, as illustrated by FIGS. 2 and 4, Stage 3 focused on further improving the yield of TCA B3.3 Stage 3. Dissolution Method and Parameters Optimization The dissolution tests were performed in "sink" conditions where the amount of solvent was at least 3 times higher than the minimum amount of solvent required for dissolution. The saturation solubilities of naltrexone in different media are listed in Table 9.

TABLE 9

The saturation solubility of Naltrexone in different media

| Sample | Solubility of API, mg/ml | Solubility in 900 ml (mg) |
|---|---|---|
| PBS pH8.0 | 0.75 | 678.520 |
| PBS pH7.4 | 0.96 | 865.141 |
| PBS pH6.0 (1:5) | 2.91 | 2617.541 |
| PBS pH5.5 (1:5) | 3.12 | 2805.860 |
| PBS pH5.0 (1:5) | 5.21 | 4690.795 |
| 20% EtOH + 80% PBS pH5.5 (1:10) | 5.73 | 5153.057 |
| Hanks' Balanced Salt solution pH8.0 | 0.65 | 580.610 |
| Hanks' Balanced Salt solution pH7.4 | 0.67 | 606.766 |
| Hanks' Balanced Salt solution pH5.0 | 0.77 | 689.409 |

The solubility of triamcinolone acetonide (TCA) in water is approximately 20 mg/L. The salting-out effect of phosphate and acetate buffer can decrease the solubility of triamcinolone acetonide (TCA). Therefore, for the next step of the dissolution method development, 20% of ethanol was added to the dissolution media with a phosphate buffer. The following dissolution media were evaluated:

10 mM phosphate buffer/20% EtOH pH 6.0

10 mM phosphate buffer/20% EtOH pH 6.5

10 mM phosphate buffer/20% EtOH pH 7.0

Results of the dissolution testing are reported in Tables 10 and 11 and FIGS. 5 and 6.

TABLE 10

Release of naltrexone from pellets in 10 mM phosphate buffer/20% EtOH at different pH (n = 1)

| Time, hrs | pH 6.0 50/75 RPM* at 37° C. | pH 6.5 50/75 RPM* at 37° C. | pH 7.0 50/75 RPM* at 37° C. |
|---|---|---|---|
| 8 | 34.11% | 31.34% | 25.87% |
| 24 | 86.61% | 79.15% | 65.36% |
| 48 | 106.77% | 106.01% | 98.43% |
| 72 | 107.17% | 104.74% | 106.86% |

Note:
*speed was accidently increased from 50 revolutions per minute (RPM) to 75 RPM at the 8th hour time point during the autosampler setup.

TABLE 11

Release of triamcinolone acetonide (TCA) from pellets in 10 mM phosphate buffer/20% EtOH at different pH

| Time, hrs | pH 6.0 50/75 RPM* at 37° C. | pH 6.5 50/75 RPM* at 37° C. | pH 7.4 50/75 RPM* at 37° C. |
|---|---|---|---|
| 8 | 33.18% | 28.58% | 23.48% |
| 24 | 87.99% | 76.69% | 64.52% |
| 48 | 109.67% | 104.85% | 98.10% |
| 72 | 109.28% | 104.64% | 107.29% |

Note:
*speed was accidently increased from 50 RPM to 75 RPM at the 8th hour time point during the autosampler setup.

B3.4 Stage 4. Dissolution Method and Parameters Optimization

Dissolution parameters: PBS buffer with 20% Ethanol at pH 7.0, 50 RPM mixing, and 37° C.

naltrexone lot #1 (length 16±0.25 mm, diameter 8.4 mm, compression pressure 5±0.5 kN, direct compression without precompression) (n=1); and naltrexone lot #2 (length 6 mm (side) or 8.68 mm from top to bottom, diameter 12 mm, compression pressure is 13.5±0.5 kN, direct compression without precompression) (n=1).

Samples were taken at 8, 24, 48, 72 and 84 hours.

Results of the dissolution testing are reported in Tables 12 and 13 and FIGS. 7 and 8.

TABLE 12

Release of naltrexone from pellets in 10 mM phosphate buffer/20% EtOH

| Time, hrs | Lot #1 | Lot #2 |
|---|---|---|
| 8 | 30.6% | 22.8% |
| 24 | 68.6% | 53.8% |
| 48 | 93.5% | 79.2% |
| 72 | 103.9% | 95.4% |
| 84 | 105.4% | 97.5% |

TABLE 13

Release of TCA from pellets in 10 mM phosphate buffer/20% EtOH at different pH

| Time, hrs | Naltrexone lot #1 | Naltrexone lot #2 |
|---|---|---|
| 8 | 27.4% | 19.2% |
| 24 | 64.7% | 48.3% |

TABLE 13-continued

Release of TCA from pellets in 10 mM phosphate buffer/20% EtOH at different pH

| Time, hrs | Naltrexone lot #1 | Naltrexone lot #2 |
|---|---|---|
| 48 | 88.9% | 73.8% |
| 72 | 100.5% | 90.3% |
| 84 | 102.5% | 92.6% |

B4. Process Development

The overall goal of the development of naltrexone (NTX) implantable pellets was to identify a process that will yield uniformly hard pellets without using excessive compression force. As NTX pellets will be used subcutaneously for long-acting indication, developing a pellet with significant hardness is desirable as hardness and dissolution are inversely related. For the development, the target hardness was 30 kg. The main process steps and variables identified during the development work are illustrated in FIG. 9.

During the compression, the following problems were observed:

Ejection of the pellets. The pellet press was not able to eject compressed pellet; and Over-compressed pellets have tendency to laminate.

Dissolution was performed for the lots of pellets. It was shown that the following parameters affect release of naltrexone:

Pellet shape: Pellets with lower surface area dissolved longer than pellets with bigger surface area;

Amount of magnesium stearate: magnesium stearate is a hydrophobic material, increased amount of magnesium stearate significantly decreases in-vitro release of the active ingredients;

Compression pressure: harder the pellet, slower the in-vitro release of the active ingredients, but if pellet is over compressed, hardness of the pellet drops significantly; and Lubrication of the die helps with pellet ejection and allows for a greater compression resulting in denser pellets.

For blend R-0954-01-032, the process used for blend R-0954-01-016 was repeated with the exception of the use of a smaller screen mesh-200 instead of a mesh-30. The observed total blend size was 300 g.

Two different lots of pellets (R-0954-01-33 and R-0954-01-34 1.5 g pellet) were compressed out of this blend as horizontal or oblong shaped pellets. The thickness ranged from 2.75-4.5 mm and the compression force ranged from 30.3 kN for 2.75 mm thick pellets to 9.92 kN for 4.5 mm thick pellet. At the higher compression forces, lamination was observed. Lot 34 consisted of oblong pellets with an average weight of 1.5 g. The thickness of these pellets ranged from 4.9 mm to 6.5 mm. The pellets laminated at higher compression forces. The final settings were a thickness of 6.5 mm and force of 16±2.5 kN. More NTX based pellets were produced, i.e., lots R-0954-01-39, R-0954-01-40, R-0954-01-41, that were all oblong in shape, based on R-095401-16 using the blends R-0954-01-38 and R-0954-01-46. The pellets of lot R-0954-01-39 were 8 mm thick with a of 10.0 mm. Pellets with higher compression resulted in pellet having a lower thickness which resulted in lamination. The pellets of lot R-0954-01-40 were 3 mm in thickness and pellets of lot R-0954-01-41 were 5.75 mm thick.

The process used to prepare blend R-0954-01-46 was similar to the process used to blend R-0954-01-38. Both blends R-0954-01-49 and R-0954-01-50 (1.5 g) were compressed from blend R-0954-01-46. The resulting pellets were oblong.

For blend R-0954-01-49, pellets with thicknesses ranging from 2.75 mm-4.0 mm were tested with compression forces ranging from 24.9 kN to 11.9 kN. For lot R-0954-01-50, pellets of 1.5 g were compressed with thicknesses ranging from 3.25-4.0 mm. It was observed that pellets with lesser thicknesses, increased compression forces. It was observed that pellets laminated at 3.0 and 3.25 mm thicknesses. Approximately 30 pellets were prepared having 3.5 mm thicknesses.

Lamination and/or pellet ejection problems were observed for all the blends produced. It was theorized that there is no optimum lubrication. To test this theory, batches of the blends were prepared with differing levels of lubrication. For example, a significant quantity of magnesium stearate (MgS) was initially added with an amount of triamcinolone acetonide (TCA) either before and/or after the selected granulation process, i.e., intra-granular and extra-granular MgS. For blend R-0954-01-55, the wall of the blender was also coated with MgS by adding excess MgS and running the blender. It was discovered, however, that pre-coating the walls of the blender did not offer adequate control of the lubrication.

The properties of a blend were driven by the different blend sizes. Magnesium stearate (MgS) is critical in determining the physical properties as well the release of naltrexone (NTX) and is required to be controlled systematically. The summaries of processes in the next phase of development are summarized in Table 14.

Variations of the lubrication steps were tested and the results are reported in Tables 15-17.

TABLE 15

| Summary of manufacturing process for different blends for NTX based pellets | |
| --- | --- |
| R-0954-01-57 (BICX-102) | R-0954-01-60 and R-0954-01-65 |
| Used blend from lot 53 | TCA (all) + equal qty of NTX (~1.0%) |
| Laminated pellets | Mix with mortar/pestle and screen through 30 mesh |
| Additional lubrication step Add 20 g MgS to the blender and blending for 1 minute (coat walls) | Add to the blender (8 quart) |
| MgS was discharged and 100 g of blend was added to the blender | Pass remaining NTX through 30 mesh |
| Blend was blended for 1 minute | Add 10% NTX to the blender and blend for 20 minutes |
| Lubrication step was repeated for the rest of the blend | Discharge blender and pass through 30 mesh |
| | Return mixture to the blender and add ~30% Blend for 20 minutes, discharge, pass through 30 mesh Add mixture to the blender and remaining NTX and blend for 20 minutes Discharge blender and pass through 30 mesh screen Return the blend to V blender and add about 20% of the total MgS Blend for 5 minutes, discharge, and screen through 30 mesh |

TABLE 14

| Summary of manufacturing process for different blends for NTX based pellets | | |
| --- | --- | --- |
| 0954-01-51 (NTX alone) | R-0954-01-53 | R-0954-01-55 (BICX 104) |
| Pass MgS through 140 mesh Transfer MgS to the V-blender | TCA/MgS Blend in mortar/pestle for 5 minutes | Used blend from lot 51 Blender was loaded with 20 g Mgs to coat the walls with MgS |
| Add 10% NTX to the blender | Pass the blend through 140 mesh screen | Mixed for 1 minute and discharged |
| Blend for 20 minutes (25 RPM) | Transfer blend to V blender | Added 100 g blend and mixed for 1 more minute |
| Discharge and pass blend through 30 mesh screen | Pass NTX through 30 mesh screen | |
| Return the blend to blender | Add 10% of NTX to the blender and blend for 20 minutes at 25 RPM | |
| Add 40% NTX | Discharge blender and pass through 30 mesh screen | |
| Blend for 20 minutes (25 RPM) Discharge and pass through 30 mesh screen | Return mixture to V blender Add 40% NTX to the V blender and blend for 20 minutes at 25 RPM | |
| Return mixture to the V blender | Discharge the V blender and pass through 30 mesh screen | |
| Add 50% NTX to the V blender | Return to V blender. Add 50% NTX to the V blender | |
| Blend 20 minutes (25 RPM) | Blend for 20 minutes at 25 RPM. | |
| Discharge V blender and pass through 30 mesh | Discharge and pass through 30 mesh screen | |
| Granulate using roller compactor | Granulate using roller compactor | |
| Note: NTX was passed through 30 mesh screen prior to adding in the steps | Force screen 140 mesh | |

TABLE 15-continued

Summary of manufacturing process for different blends for NTX based pellets

| R-0954-01-57 (BICX-102) | R-0954-01-60 and R-0954-01-65 |
|---|---|
| | Granulate using roller compactor |
| | Force screen blend through 40 mesh screen |
| | Transfer blend to the V blender and add remaining MgS |
| | Blend for additional 5 minutes (125 RPM) |
| | Discharge blender |

TABLE 16

Summary of manufacturing process for different blends for NTX based pellets
R-0954-01-71 and R-0954-01-76

Mix TCA (all) + Mg S (~80% of required qty) in mortar and pestle for 5 min
Pass the blend through 140 mesh screen
Dry clean 140 mesh screen with 10% NTX. Mix TCA, MgS, NTX in V blender for 20 min (25 RPM)
Discharge V blender and pass the mixture through 30 mesh screen
Add 40% of the total NTX and mix in blender for 20 min
Discharge the V blender and pass the blend through 30 mesh screen
Add remaining amt of NTX and blend for additional 20 min at 25 RPM
Discharge the V blender
Pass the mix through roller compactor
Add granulated blend to V blender and add 20% MgS (extra granular)
Note: NTX is passed through 30 mesh prior to using in the process

TABLE 17

Summary of manufacturing process for different blends for NTX based pellets
R-0954-01-68 (Placebo implant)

Weigh and transfer spray dried lactose and cholesterol to the robot coupe
Mix the blend for 1 min at 500 rpm, followed by mixing at 2000 rpm for 30 sec each
Add magnesium stearate and mix manually
Transfer TCA to the blend and mix for 30 sec at 1000 rpm in robot coupe
Pass the blend through 30 mesh screen
Compress Blend 0954-01-51 was manufactured without the addition of triamcinolone acetonide (TCA), as pellets comprised of naltrexone (NTX) without any additional ingredients would be likely candidates for clinical trials. The manufacturing steps for producing blend 0954-01-51 were similar to the steps to produce blend R-0954-01-16, except in the $1^{st}$ step, only magnesium stearate (MgS) was used. Pellets made from blend R-0954-01-55 were prepared by using blend R-0954-01-051. A 10 mm flat face tooling instrument was used during the compression step. Final settings for these pellets are listed in Table 18.

TABLE 18

Compression parameters for pellets (R-0954-01-55)

| Force set point | 16 kN |
|---|---|
| Thickness | 9.75 mm |
| Dosing | 19.5 mm |
| Feeder | 15 RPM |
| Precompression mode | 6.45 mm for 10 sec |
| Shaker | 10 sec 50 msec |

About 300 pellets were manufactured, de-dusted, packaged and sent for sterilization by gamma-irradiation.

Blend R-0954-01-053 was prepared containing naltrexone (NTX) and triamcinolone acetonide (TCA) using the same procedures for blends R-0954-01-38 and R-0954-01-46 with a total blend size of 500 g. Blend R-0954-01-57 was prepared using blend R-0954-01-53.

For blend R-0954-01-57 (Table 15), an additional lubrication step was performed where about 20 g of magnesium stearate (MgS) was added to the blender and blended for 1 min to coat the walls thereof. MgS was discharged and 100 g of blend R-0954-01-53 was added to the blender and the lubrication step was repeated for the rest of the blend. Pellets with compression force of up to 18 kN were acceptable, but 21.75 kN were over-compressed. The force set point was 15.3 kN (although it may range from 13.6 kN±5% to 18.2 kN±5%, thickness set point was 9.85 mm and the dosing set point was 20.51 mm. About 400 pellets were manufactured, packaged, and sent for sterilization.

For blend R-0954-01-60 that contains a mixture of naltrexone (NTX) and triamcinolone acetonide (TCA), the production process was modified by including the additional steps of adding approximately 20% MgS (intragranular) before roller compaction step and approximately 80% MgS to the granulated blend (extra-granular) after the compaction step. Extra-granular MgS aids in lubrication of the pellet press during manufacturing. The thickness testing varied from 9.25 to 9.65 mm and the compression forces ranging from 13.6 kN-19.6 kN±5%.

Approximately, 80% intragranular magnesium stearate (MgS) was added to blend R-0954-01-71 before roller compaction and 20% extra-granular blend. The subsequent steps were similar to the overall manufacturing process where naltrexone (NTX) was addressed in geometric progression and the blend was screened before the addition of NTX.

Batch R-0954-01-76 were manufactured using similar procedures used to manufacture the R-0954-01-71 pellets wherein 80% of the MgS was added intra-granularly and remaining 20% was added post granulation (extra-granular). Differing die dwell times were tested to optimize the hardness and porosity of the pellets. The pellet press required advanced settings to reduce or eliminate compression force decay while the pellets are being compressed. The inventors consulted with the pellet press manufacturer (Natoli® Engineering Co., Inc., St. Charles, MO) for the advanced settings. Lots R-0954-01-55, R-0954-01-57, R-0954-01-63, R-0954-01-67, R-0954-01-73 and R-0954-01-74 were tested for use in good laboratory practices (GLP) animal studies. The lead was determined based on the results of the in vivo testing.

B5. Container-Closure System

For the clinical development work, pellets were packaged in 5 mL BD Luer-Lok™ sterile parenteral grade syringes (Becton, Dickinson and Company, Franklin Lakes, NJ). The filled syringes were placed within self-sealing pouches GS Medical Packaging, Inc. (GS Medical Packaging, Inc., Etobicoke, ON, CA).

B6. Sterilization

The naltrexone implants were processed in ExCell® precision irradiator (SteriGenics® U.S., Oak Brook, IL at ambient temperature. The processing chamber is pre-dose mapped for various densities/geometries and the absorbed doses are calculated by placing 2 dosimeters on the outside and applying adjustment factors to the recorded doses. Each run had a 25-40 kGy dose range.

B7. Stability Testing

Compatibility with the dosage device: The solid implantable pellet is placed within the sterile syringes. The interaction of the solid pellet with the syringe device was not expected. Stability data for 7 months at room temperature and accelerated conditions (40° C./75% RH) for lots R-0954-01-55 (NTX alone), lot R-0954-01-67 (NTX/TCA combination) and placebo (TCA alone) are reported in Table 19.

TABLE 19

| Lot Number | Blend lot# | Pellet description | Medias used (number of pellets) |
|---|---|---|---|
| R-0954-01-03/05 | R-0954-01-01 | 8.4 mm; ~17 kg (old tester) | Water pH 5.5, 50 RPM, 37° C. (1)<br>Water pH 5.5, 60 RPM, 60° C. (1)<br>Water pH 5.5, 150 RPM, 37° C. (1)<br>Water + EtOH 80/20 v/v, 50 RPM, 37° C. (1)<br>0.1% SLS in water, 50 RPM, 37° C. (1)<br>0.05N HCl, pH 1.0, 50 RPM, 37° C. (1)<br>20 mM Acetate Buffer, pH 3.8, 50 RPM, 37° C. (1)<br>10 mM Acetate Buffer, pH 3.8, 50 RPM, 37° C. (1)<br>10 mM Acetate Buffer, pH 5.0, 50 RPM, 37° C. (1)<br>10 mM Acetate Buffer, pH 5.8, 50 RPM, 37° C. (1)<br>PBS, pH 5.0, 50 RPM, 37° C. (1)<br>PBS, pH 6.0, 50 RPM, 37° C. (1)<br>PBS, pH 7.4, 150 RPM, 37° C. (1)<br>PRS, pH 7.4, 50 RPM, 37° C. (1) |
| R-0954-01-12A | R-0954-01-01 | 8.4 mm; ~32 kg (old tester) | PBS + EtOH 80/20 v/v, pH 7.0 50 RPM, 37° C. (1) |
| R-0954-01-12B | R-0954-01-01 | 12 mm; ~35 kg (old | PBS + EtOH 80/20 v/v, pH 7.0 50 RPM, 37° C. (1) |
| R-0954-01-19 (passed through 80 mesh) 35 mg | | 8.4 mm; ~35 kg (old tester) | PBS, pH 7.4, 50 RPM, 37° C. (3)<br>PBS + EtOH 80/20 v/v, pH 7.0 50 RPM, 37° C. (1)<br>Hank's buffer pH 7.4 50 RPM, 37° C. (3) |
| R-0954-01-20 (passed through 40 | | 8.4 mm; ~11.75 kg (old tester) | PBS, pH 7.4, 50 RPM, 37° C. (1)<br>PBS + EtOH 80/20 v/v, pH 7.0 50 RPM, 37° C. (1) |
| R-0954-01-23A (passed through 40 | R-0954-01-16 | 10 mm; ~35 kg (old tester) Die lubrication | PBS, pH 7.4, 50 RPM, 37° C. (3)<br>PBS + EtOH 80/20 v/v, pH 7.0 50 RPM, 37° C. (1) |
| R-0954-01-23B (passed through 40 | | 10 mm; ~10.2 kg (old tester) | PBS, pH 7.4, 50 RPM, 37° C. (1)<br>PBS + EtOH 80/20 v/v, pH 7.0 50 RPM, 37° C. (1) |
| R-0954-01-24 (passed through 80 | | 8.4 mm; ~17 kg (old tester) | PBS, pH 7.4, 50 RPM, 37° C. (3)<br>PBS + EtOH 80/20 v/v, pH 7.0 50 RPM, 37° C. (1) |
| R-0954-01-25 (passed through 80 | | 10 mm; ~15 kg (old tester) | PBS, pH 7.4, 50 RPM, 37° C. (1)<br>PBS + EtOH 80/20 v/v, pH 7.0 50 RPM, 37° C. (1) |
| R-0954-01-27 (passed through 80 | | 9.5 mm; ~9.6 kg (old tester) | PBS, pH 7.4, 50 RPM, 37° C. (1)<br>PBS + EtOH 80/20 v/v, pH 7.0 50 RPM, 37° C. (1) |
| R-0954-01-30 (passed through 40 | | oblong | PBS + EtOH 80/20 v/v, pH 7.0 50 RPM, 37° C. (3) Hank's buffer pH 7.4 50 RPM, 37° C. (3) |
| R-0954-01-33 | R-0954-01-32 | oblong | PBS, pH 7.4, 50 RPM, 37° C. (3)<br>Hank's buffer pH 7.4 50 RPM, 37° C. (3) |
| R-0954-01-34 1.5 g pellet | | oblong | PBS, pH 7.4, 50 RPM, 37° C. (3)<br>Hank's buffer pH 7.4 50 RPM, 37° C. (3) |
| R-0954-01-36 | | | PBS, pH 7.4, 50 RPM, 37° C. (3) |
| R-0954-01-37 | | 08.4 mm, 17.2 kg | PBS, pH 7.4, 50 RPM, 37° C. (3)<br>Hank's buffer pH 7.4 50 RPM, 37° C. (3) |
| R-0954-01-39 | R-0954-01-38 | 012.5 mm (biconvex), 22.75 kg | PBS, pH 7.4, 50 RPM, 37° C. (3)<br>Hank's buffer pH 7.4 50 RPM, 37° C. (3) |
| R-0954-01-40 | | 010 mm, 17.3 kg | PBS, pH 7.4, 50 RPM, 37° C. (3)<br>Hank's buffer pH 7.4 50 RPM, 37° C. (3) |
| R-0954-01-49 | R-0954-01-46 | Oblong, 3.25 mm thick, 16.6 kg | PBS, pH 7.4, 50 RPM, 37° C. (3)<br>Hank's buffer pH 7.4 50 RPM, 37° C. (3)<br>PBS + EtOH, pH 7.4, 50 RPM, 37° C. (3) |
| R-0954-01-50 | | Oblong, 3.5 mm, 21.54 kg | — |
| R-0954-01-55 | R-0954-01-51 | 010 mm, 26.5 kg (old tester) and 17.8 kg with new tester | Hank's buffer pH 7.4. (50 RPM stir rate) |

TABLE 19-continued

Summary of dissolution testing on different lots

| Lot Number | Blend lot# | Pellet description | Medias used (number of pellets) |
|---|---|---|---|
| R-0954-01-57 | R-0954-01-53 | Length 10.2-10.5 mm flat face, 15.85 kg with new tester and 28.8 kg with | Hank's buffer pH 7.4. (50 RPM stir rate) |
| R-0954-01-63 | R-0954-01-60 | Length 10.2-10.5 mm flat face, 25.9 kg, higher than 35 (old | Hank's buffer pH 7.4. (50 RPM stir rate) |
| R-0954-01-67 | R-0954-01-65 | Length 10.2-10.5 mm flat face, 25-26 kg new tester and more than 35 kg with the old | Hank's buffer pH 7.4. (50 RPM stir rate) PBS + 20EtOH pH 5.5 |
| R-0954-01-73 | R-0954-01-71 | 20.68 | 80% PBS/20% EtOH at pH 5.5 |
| R-0954-01-74 | R-0954-01-72 | 24.71 kg | 80% PBS/20% EtOH at pH 5.5 |

C. Therapeutic Uses of Naltrexone Implants and Proof of Concept

Various embodiments of the present disclosure generally relate to a subcutaneous biodegradable medical implant comprising relatively pure naltrexone (e.g., naltrexone hydrochloride, naltrexone base, naltrexone anhydrous base) without triamcinolone acetonide (TCA) and with less than 2% magnesium stearate that, when implanted in a patient, aids in treatment of a disease or disorder in the patient, such as impulse control and behavioral disorders. Implants of the disclosure are useful in treating addiction disorders, including but not limited to Opioid Use Disorder (OUD), Alcohol Use Disorder (AUD) and opioid and/or alcohol addictions, food addiction, pornography addiction, methamphetamine, gambling addiction, gaming addiction, sex addiction, screen (computer/internet) addiction, work addiction, exercise addiction, spiritual addiction, shopping addiction, harm-to-self addictions (cutting), social media addiction, or obsessive-compulsive disorder. Implants of the disclosure are useful in treating obesity, weight gain, and weight gain associated with hypothyroidism, Hashimoto's thyroiditis, polycystic ovary syndrome (PCOS), or sleep apnea. Implants of the disclosure are useful in treating chronic pain, inflammation, and complex regional pain syndrome.

C1. Animal Studies-Preliminary

The potential toxicity of the test articles, BICX102 and BICX104, was tested. Both were administered as subcutaneous implants into Yucatan minipigs (BioChemed Services, Winchester, VA to evaluate the potential reversibility of any findings. In addition, the toxicokinetic (TK) characteristics of BICX102 and BICX104 were determined. Naltrexone subcutaneous pellets (implants) BICX102 is comprised of naltrexone and triamcinolone acetonide (TCA) as the pharmaceutical ingredients. BICX104 is naltrexone as the pharmaceutical ingredient without triamcinolone acetonide (TCA). Both, BICX102 and BICX104 contain small amounts of magnesium stearate as an excipient, primarily as a lubricant. BICX102 and BICX104 are currently under development for the treatment of alcohol and opioid use disorders. The details of the aforementioned in vivo studies are set forth in Table 20.

TABLE 20

| | No. of Animals | | TA | | Necropsy (No. of Animals) | | | |
|---|---|---|---|---|---|---|---|---|
| | | Re-Implanted on | TA | Implanted on | | | | |
| Group No. | Implanted on Day 1 (M/F) | Day 91 ± 2 and Day 182 ± 2 (M/F) | Implanted on the One Side | the Contralateral Side | Main Day 91 ± 2 (M/F) | Recovery Day 182 ± 1 (M/F)[a] | Main Day 273 ± 3 (M/F)[b] | Recovery Day 365 ± 3 (M/F)[c] |
| 1[d] | 12/12 | 6/6 | One Placebo Containing 11 mg of Magnesium Stearate | One Placebo Containing 10 mg of TCA[f] and 11 mg of Magnesium Stearate | 4/4 | 2/2 | 4/4 | 2/2 |
| 2[d] | 12/12 | 6/6 | One BICX104 containing 1 g of naltrexone and 11 mg Magnesium Stearate | One Sham PTFE (Only animals receiving a single implant procedure) | 4/4 | 2/2 | 4/4 | 2/2 |

Experimental Design[g]

TABLE 20-continued

| | No. of Animals | | TA | | Necropsy (No. of Animals) | | | |
|---|---|---|---|---|---|---|---|---|
| | | Re-Implanted on | TA | Implanted on | | | | |
| Group No. | Implanted on Day 1 (M/F) | Day 91 ± 2 and Day 182 ± 2 (M/F) | Implanted on the One Side | the Contralateral Side | Main Day 91 ± 2 (M/F) | Recovery Day 182 ± 1 (M/F)[a] | Main Day 273 ± 3 (M/F)[b] | Recovery Day 365 ± 3 (M/F)[c] |
| 3[d] | 12/12 | 6/6 | One BICX102 containing 1 g of naltrexone with 11 mg Magnesium Stearate and 10 mg TCA[f] | One Sham PTFE (Only animals receiving a single implant procedure) | 4/4 | 2/2 | 4/4 | 2/2 |
| 4[d] | 12/12 | 6/6 | Two BICX102 containing 1 g of naltrexone with 11 mg Magnesium Stearate and 10 mg TCA[f] in separate pockets | Two Sham PTFE in separate pockets (Only animals receiving a single implant procedure) | 4/4 | 2/2 | 4/4 | 2/2 |
| 5[d] | 12/12 | 6/6 | Twelve BICX102 containing 1 g of naltrexone with 11 mg Magnesium Stearate and 10 mg TCA[f] (two pellets per pocket for a total of six pockets) | Two Sham PTFE in one pocket (Only animals receiving a single implant procedure) | 4/4 | 2/2 | 4/4 | 2/2 |
| 6 | 6[e]/6[e] | — | Two BICX102 containing 1 g of naltrexone with 11 mg Magnesium Stearate and 10 mg TCA[f] in separate pockets | Two Sham PTFE in separate pockets | See Note[e] Below | — | — | — |

[a]Animals implanted on Day 1 and maintained until Day 182 ± 1

[b]Animals were/will be dosed on Days 1, 91 ± 2, and 182 ± 2.

[c]Animals were/will be dosed on Days 1, 91 ± 2, and 182 ± 2 and maintained until Day 365 ± 3

[d]Side of implantation alternated at each surgical procedure.

[e]Acute Phase animals (4/sex) were submitted for necropsy on Day 14 following implantation for the main acute terminal animals, and 2 animals/sex for Recovery necropsy were submitted for necropsy on Day 30.

[f]Triamcinolone acetonide (TCA)

[g]This table includes the experimental design for the entire duration of the study; however, this interim report only includes data collected through the Day 182 ± 1 necropsy.

Based upon the results included in this interim report, it was surprisingly discovered that the BICX104 implant had no observable adverse effect level (NOAEL) in Yucatan minipigs. The establishment of the NOAEL was based on the absence of any systemic effects and upon the non-adversity of the microscopic findings.

C2. Study Design

The potential toxicity of BICX102 and BICX104, when given as a subcutaneous implant to minipigs was studied. In addition, the potential reversibility of any findings, was evaluated. Also, the toxicokinetic (TK) characteristics of BICX102 and BICX104 were determined. Both are naltrexone subcutaneous implants; BICX102, with naltrexone and triamcinolone acetonide (TCA) as the pharmaceutical ingredients; and BICX104, with naltrexone as the pharmaceutical ingredient only. Both also include magnesium stearate as an excipient, for lubricating purposes, and both are currently under development for the treatment of alcohol and/or opioid use disorders.

C3. Test Article. Placebo Article, and Inert Article Identification

TABLE 21

| | | | Test Article Identification | | |
|---|---|---|---|---|---|
| Identification | BICX104 | BICX102 | BICX102 | BICX102 | BICX102 | BICX102 |
| Alternate Identification | BICX102 without TCA | — | — | — | Naltrexone + TCA Pellets (Implants) | Naltrexone + TCA Pellets (Implants) |
| Batch (Lot) No. | R-0954-01-55 | R-0954-01-57 | R-0954-01-63 | R-0954-01-67 | R-0954-01-73 | R-0954-01-74 |

TABLE 22

Placebo and Inert Article Identification

| Identification | Placebo (11 mg MgS only) | Placebo (11 mg MgS and 10 mg TCA | PTFE Sham implant |
|---|---|---|---|
| Batch (Lot) No. | R-0954-01-69 | R-0954-01-70 | 58973 |
| Expiration/Retest Date | Not available | Not available | 4 Feb. 2022 |

TABLE 23

Procedure-related Medications and Dose Levels

| Medication | Interval, Dose Level, and Route Surgery (Day 1, 91 ± 2, and 182 ± 2) |
|---|---|
| Acepromazine | 0.1 to 1 mg/kg IM |
| Atropine | 0.05 mg/kg IM |
| Carprofen (or Meloxicam[f]) | 2 mg/kg IM (or 0.4 mg/kg SC) |
| Dopram[c] | 1 to 2 mL IV |
| Nocita | 5.3 mg/kg INF |
| Excede | 6.6 mg/kg IM |
| Cerenia[d] | 0.5 mg/kg SC PRN |
| Telazol[a,b] | 3 to 4 mg/kg IM |
| Isoflurane | To effect INH |
| LRS | 110 to 380 mL/hour IV |
| Saline[e] | 20 mL IV |

[a]Added to 5 mL of sterile water.
[b]Additional administered as needed.
[c]Administered to 1 Group 5 male (Animal No. 5002). 1 Group 6 male (Animal No. 6006), and 1 Group 2 male (Animal No. 2006) during the Day 1 surgery.
[d]Administered as needed to some animals.
[d]Administered to 1 Group 6 male (Animal No. 6006) during the Day 1 surgery.
[f]Additional 4 mL was administered to 1 Group 5 female (Animal No. 5505)
IM-Intramuscular
PRN-As needed
INF-Infused into incisions
LRS-Lactated Ringer's solution
INH-Inhalation
IV-Intravenous
SC-Subcutaneous C4. Surgical Procedure Skin incisions were made in the pre-scapular region of the neck/withers (approximately 1.5 cm in length); discrete subcutaneous pockets were created using a 10.5 mm trocar. Skin incisions made in the abdomen were approximately 1.5 cm in length; discrete subcutaneous pockets were created using a 10.5 mm trocar. The corners of an approximately 5×4 cm or 5×5 cm square were tattooed around the appropriate left or right implant sites (pre-scapular or abdominal region). The incisions were closed using absorbable suture and the skin closed with tissue glue. Digital photographs were taken.

C5. Justification of Route and Dose Levels

Implantation is the intended route of administration of this test article in humans. The dose levels were selected based on information provided by the Inventor indicating that the human clinical dose is 1 to 2 g of naltrexone (NTX), and 10 to 20 mg of triamcinolone acetonide (TCA) and 11 to 22 mg of magnesium stearate (MgS) per subcutaneous implant that is slowly released over 3 months (90 days) which is equivalent to a 11 to 22 mg/kg/day NTX dose and 0.11 to 0.22 mg/kg/day TCA dose.

C6. Body Weight and Body Weight Change

Implantation of the test article was not associated with any effects on body weight values over the course of the study. Animals gained weight at approximately the same rate over the 182-day period included in this report. Occasional differences from controls were noted but were of low magnitude and considered to reflect normal biological variation.

C7. Skin Reaction

All placebo, PTFE, and test article implantation sites were observed with very slight erythema and very slight edema on at least one occasion. The number of occurrences of erythema and edema were increased in implantation sites that received BICX102 (regardless of the number of sites or implants per site), but much less so for BICX104, the formulation that did not contain triamcinolone acetonide (TCA). Scores greater than very slight erythema were noted on occasion and were typically transient in nature resolving by the next observation interval. As the majority of skin reaction scores were very slight (barely perceptible) the increase in occurrence in test-article implanted sites is considered non-adverse due to the low severity.

Group 2 was observed with an increase in the mean score for severity of edema, which was attributable to a single animal (Animal No. 2505) that was receiving veterinary treatment for significant swelling of the implantation site along with other observations that were indicative of a possible infection and was thus not considered test article related. Following a single subcutaneous implant of 1 g NTX (Group 2) and 1 g NTX with 10 mg TCA (Group 3), individual $C_{max}$ and AUC values appeared to be similar. Systemic exposure to NTX did not appear to be impacted when administered with TCA.

C8. Implant Sites (up to Day 91±2 Necropsy)

Test article-related microscopic findings at the implant site occurred on Day 14±2, 28±2, and 91±2 at all BICX102 and BICX104 implant sites compared to PTFE sham implant (Day 14±2 and 28±2) and/or MgS placebo, TCA/MgS placebo or PTFE sham implants (Day 91±2). In general, BICX102 associated implant sites had greater inflammatory cell infiltrate and localized tissue response (necrosis, hemorrhage, crust, ulceration, bacterial infiltration) compared to BICX104, and the various placebo or sham controls. MgS and TCA/MgS placebo implants also had greater inflammatory cell infiltrate and localized tissue response when compared to PTFE sham implant.

Adipose tissue at the implant site was evaluated and no overt changes in adipocyte character were noted outside of the inflammatory cell infiltrates and localized tissue responses noted below.

C9. Implant Sites (Day 91±2 Necropsy)

Test article-related microscopic findings were evaluated for the three test article implant conditions: single BICX102, double BICX102 (two BICX102 implants in a single pocket), and single BICX104. Test article implants were compared to placebo magnesium stearate (MgS), placebo triamcinolone acetonide (TCA)/magnesium stearate (MgS), sham implant (PTFE), double sham implants (two PTFE implants in a single pocket), and control (normal skin). All implanted sites examined had some amount of leukocyte infiltration and associated findings, though the incidence, composition and density varied. In general, BICX102 and double BICX102 implant sites had greater individual cell and total cell infiltrates than the various placebo groups and a more severe localized tissue response (necrosis, mineralization, fibrosis, etc.). BICX104, the TCA and MgS placebo implant sites were roughly equivalent and consistently had greater cellular infiltrate than PTFE. BICX102 and BICX104 implant sites also had fibrosis, mineralization, or central cavitation, which were not consistently present in MgS and TCA/MgS placebo implant sites.

BICX102 and double BICX102 implants had increased neutrophilic infiltration, increased necrosis, increased overall cell parameters, increased mineralization, increased fibrosis, the presence of cavitation with an eosinophilic core, increased erosion/crust/ulceration, increased thrombi in small vessels, occasional squamous metaplasia of the implant pocket, bacterial infiltration, and increased hemorrhage compared to placebos (MgS and TCA/MgS) and PTFE. When compared to BICX104; BICX102 and double BICX102 implant sites had increased neutrophils, lymphocytes, necrosis, and overall total cells with decreased giant cells, increased non-cellular parameters included erosion/crust/ulceration, thrombi, metaplasia, and bacterial infiltration.

TABLE 24

BICX102/BICX104 Comparison

Males

| Day 91 ± 2 | Normal Skin | BICX102 × 1 site | BICX102 × 2 sites | BICX102 × 6 sites MFD 2/pocket | BICX104 × 1 site |
|---|---|---|---|---|---|
| Increased Neutrophils[1] | 0 | 3.5 | 3.0 | 3.6 | 1.8 |
| Increased Lymphocytes[1] | 0 | 2.8 | 2.9 | 2.1 | 2.0 |
| Increased Necrosis[1] | 0 | 3.3 | 2.4 | 3.0 | 1.5 |
| Increased Total Cell[1] | 0 | 29.0 | 26.9 | 27.9 | 22.0 |
| Giant cells[1] | 0 | 0.3 | 0.7 | 0.5 | 1.5 |
| Erosion/ulcer[2] | 0 | 2 | 5 | 5 | 0 |
| Thrombus[2] | 0 | 1 | 0 | 7 | 0 |
| Squamous metaplasia[2] | 0 | 1 | 0 | 2 | 0 |
| Bacteria[2] | 0 | 1 | 3 | 4 | 0 |

[1]Represented as mean.
[2]Represented as number present.
The scale for necrosis was 0-4. (1 = minimal, 2 = mild, 3 = moderate and 4 = severe)

TABLE 25

BICX102/BICX104 Comparison

Females

| Day 91 ± 2 | Normal Skin | BICX102 × 1 site | BICX102 × 2 sites | BICX102 × 6 sites MFD 2/pocket | BICX104 × 1 site |
|---|---|---|---|---|---|
| Increased Neutrophils[1] | 0 | 3.3 | 4.0 | 3.5 | 1.3 |
| Increased Lymphocytes[1] | 0 | 2.8 | 2.3 | 2.1 | 2.8 |
| Increased Necrosis[1] | 0 | 2.8 | 3.9 | 3.4 | 0.5 |
| Increased Total Cell[1] | 0 | 27.0 | 29.8 | 28.2 | 18.5 |
| Giant cells[1] | 0 | 0.3 | 0 | 0.2 | 0.8 |
| Erosion/ulcer[2] | 0 | 2 | 7 | 8 | 0 |
| Thrombus[2] | 0 | 3 | 6 | 21 | 0 |
| Squamous metaplasia[2] | 0 | 0 | 0 | 0 | 0 |
| Bacteria[2] | 0 | 1 | 7 | 8 | 0 |

[1]Represented as mean.
[2]Represented as number present.

C10. Implant Sites (up to Day 182±2 Necropsy)

Test article-related microscopic findings were evaluated for the three test article implant conditions: Single BICX102, double BICX102 (two BICX102 implants in a single pocket), and single BICX104. Test article implants were compared to placebo magnesium stearate (MgS), placebo MgS with triamcinolone acetonide (TCA), sham implant (PTFE), double sham implants (two PTFE implants in a single pocket), and control (normal skin). All implanted sites examined had some amount of leukocyte infiltration and associated findings, though the incidence, composition and density varied. BICX104 evaluation was limited to a single implant site/sex/group which limited interpretation of this test condition at this time point. In general, BICX102 and BICX104 associated implant sites had comparable localized tissue response in males and increased inflammatory cell infiltrates and localized tissue response in females compared to placebo and sham controls.

Adipose tissue at the implant site was evaluated and no overt changes in adipocyte character were noted outside of the inflammatory cell infiltrates and localized tissue responses noted below.

In males, BICX102 and double BICX102 implants generally had similar or decreased total cell infiltrates and decreased incidence of central core of eosinophilic material with increased incidence of mineralization and focal epidermal hyperplasia compared to PTFE and placebos (MgS and MgS with TCA). Necrosis was variable across BICX102 implant sites. In general, the single BICX102 implant had variably increased necrosis compared to single PTFE implant and placebos, while the double BICX102 implant sites had decreased necrosis when compared to the double PTFE implant. The effect of inherent instability and mechanical trauma of double implants on the necrosis in the double implantation sites was uncertain.

ence of bacterial colonies when compared to control skin, magnesium stearate (MgS) placebo, triamcinolone acetonide (TCA) placebo, and PTFE sham implant. Test article-related systemic microscopic findings were limited to the adrenal gland and thymus of Group 5 animals. Minimal to moderate adrenocortical atrophy and mild to marked thymic lymphoid depletion were identified microscopically, correlating with decreased organ weights in this group. These findings in Group 5 are likely systemic manifestations related to the increased, cumulative dose of triamcinolone acetonide (TCA) present in implants.

BICX104 implant has been established as a no observable adverse effect level (NOAEL) in Yucatan minipigs. The establishment of the NOAEL was based on the absence of any systemic effects and upon the non-adversity of the microscopic findings.

TABLE 26

| BICX102/BICX104 Comparison | | | | |
| --- | --- | --- | --- | --- |
| | Males | | | |
| Day 182 ± 2 | Normal Skin | BICX102 × 1 site | BICX102 × 2 sites | BICX102 × 6 sites MFD two per pocket | BICX104 × 1 site |
| Neutrophils[1] | 0 | 2.0 | 1.0 | 0.9 | 0 |
| Lymphocytes[1] | 0 | 2.5 | 1.3 | 1.8 | 3.0 |
| Macrophage[1] | 0 | 2.5 | 1.8 | 1.6 | 3.0 |
| Necrosis[1] | 0 | 2.0 | 0 | 0.3 | 0 |
| Total cell[1] | 0 | 22.0 | 11.5 | 10.0 | 14.0 |
| Neovascularization[2] | 0 | 2 | 2 | 7 | 0 |
| Mineralization[2] | 0 | 1 | 2 | 0 | 0 |
| Foreign material[2] | 0 | 0 | 1 | 1 | 0 |
| Central cavitation[2] | 0 | 2 | 2 | 1 | 0 |
| Focal epidermal hyperplasia[2] | 0 | 1 | 1 | 2 | 0 |

[1]Represented as mean.
[2]Represented as number present.

TABLE 27

| BICX102/BICX104 Comparison | | | | |
| --- | --- | --- | --- | --- |
| | Females | | | |
| Day 182 ± 2 | Normal Skin | BICX102 × 1 site | BICX102 × 2 sites | BICX102 × 6 sites MFD two per pocket | BICX104 × 1 site |
| Neutrophils[1] | 0 | 3.0 | 1.7 | 3.4 | 0 |
| Lymphocytes[1] | 0 | 3.0 | 2.3 | 2.3 | 3.0 |
| Macrophage[1] | 0 | 4.0 | 3.3 | 2.9 | 4.0 |
| Necrosis[1] | 0 | 4.0 | 2.0 | 3.7 | 0 |
| Total cell[1] | 0 | 38.0 | 25.3 | 25.8 | 24.0 |
| Neovascularization[2] | 0 | 2 | 3 | 2 | 0 |
| Mineralization[2] | 0 | 2 | 2 | 12 | 0 |
| Serocellular crust[2] | 0 | 0 | 0 | 1 | 0 |
| Bacteria[2] | 0 | 0 | 0 | 1 | 0 |

[1]Represented as mean.
[2]Represented as number present.

At Day 91±2, test article-related microscopic findings associated with BICX102, double BICX102, or BICX104 implants consisted of variable inflammation (with leukocyte population of varying severity), necrosis (notably increased in BICX102 implant conditions), fibrosis, hemorrhage, erosion/ulceration, serocellular crust formation, and the pres- D. Alternative Formulations Cholesterol in an implant slows the release of the naltrexone active ingredient. An amount of cholesterol is chosen to balance the rate of release of the naltrexone from the pellet into the bloodstream of the patient over the lifetime of the pellet and to minimize the amount of remaining cholesterol in the pellet after all or most of the naltrexone is released. That is, for a given indication, the amount of cholesterol in the implant or pellet is chosen such that there is not an excess of cholesterol remaining toward the end of a lifetime of the pellet such that a less than ideal or preferred amount of naltrexone is released into or absorbed into the bloodstream of the patient toward the lifetime of the pellet (e.g., too much cholesterol may inhibit the sustained release of naltrexone). At the same time, for a given indication, an amount of cholesterol in the implant or pellet is chosen such that enough cholesterol remains surrounding the pellet of naltrexone to allow for a desired release or absorption of naltrexone over the lifetime of the pellet (e.g., too little cholesterol may result in too high of a release of naltrexone at any given point in time during the lifetime of the pellet, and especially toward the lifetime of the pellet). Pellets having 10% or more of cholesterol may lead to an increase in remnant residue in a patient as well as an undesirable increase in total pellet mass (e.g., this may inhibit a more desirable smaller pellet without an added benefit). It is recommended that less than 10% of the implant consist of cholesterol, preferably around 2%. An embodiment of the present invention consists of an implant comprised of 0.1 to 5.0 grams±5% by weight, between 1.0 and 1.5±5% by weight, or between 200 mg and 500 mg±5% by weight, of naltrexone base, 2 mg magnesium stearate and 4 mg cholesterol with or without 2 mg triamcinolone acetonide (TCA), preferably without triamcinolone acetonide (TCA). If triamcinolone acetonide (TCA) is present in the formulation, the acetonide form is used in amounts ranging from 0.1 to 100 mg±5%. A preferred embodiment of the present invention consists of an implant comprised of 200 mg of naltrexone base, 2 mg magnesium stearate and 4 mg cholesterol with or without 2 mg triamcinolone acetonide (TCA), preferably without triamcinolone acetonide (TCA).

Example pellets of the present disclosure may comprise less than 10% cholesterol by weight. Some implants comprise less than 9%, less than 8%, less than 7%, less than 6%, less than 5%, less than 4%, less than 3%, less than 2%, or less than 1% cholesterol. Some implants comprise 0.5%, 1%, 1.5%, 2%. 2.5%. 3%, 3.5%, 4%, 4.5, 5%, 5.5%, 6%, 6.5%, 7%, 7.5%, 8%, 8.5%, 9%, or 9.5% cholesterol. Some embodiments comprise 2% cholesterol. Some embodiments comprise 1% magnesium stearate, 1% triamcinolone acetonide (TCA), and 2% cholesterol. Some implants/pellets comprise a cholesterol coating. Some implants/pellets comprise a partial coating of cholesterol on the exterior of the implant/pellet to slow an initial burst of the naltrexone active ingredient. Some embodiments comprise 1% magnesium stearate, 1% triamcinolone acetonide (TCA) and 2% cholesterol. Some embodiments comprise 200 mg naltrexone base, 2 mg triamcinolone acetonide (TCA) (steroid active ingredient), 2 mg magnesium stearate, and 4 mg cholesterol.

In some embodiments, the implant releases dosage amount(s) of naltrexone into a bloodstream of the patient. In embodiments, the dosage amount(s) of naltrexone can be in an amount within the range of 150 mg to 5 g. In some embodiments, the dosage amount(s) of naltrexone is in an amount of 200 mg, 400 mg, 1 g, 1.1 g, 1.2 g, 1.3 g, 1.4 g, or 1.5 g. In some embodiments, the dosage amount(s) of naltrexone is in an amount of 2.2 g. The amount of naltrexone in a pellet varies from 150 mg to 5 g naltrexone per pellet and more usually from 200 mg-1.4 g per pellet. Some pellets comprise 200 mg, 400 mg, 1.1 g, or 1.4 naltrexone. In some embodiments, the dosage amount(s) of naltrexone can be in an amount within the range of 250 mg to 4 g, 300 mg to 4 g, 350 mg to 4 g, 400 mg to 4 g, 450 mg to 4 g, 500 mg to 4 g, 550 mg to 4 g, 600 mg to 4 g, 650 mg to 4 g, 700 mg to 4 g, 750 mg to 4 g, 800 mg to 4 g, 850 mg to 4 g, 900 mg to 4 g, 950 mg to 4 g, 1 g to 4 g, 1.1 g to 4 g, 1.5 g to 4 g, 2 g to 4 g, 2.2 g to 4 g, 2.2 g to 3 g, 2 g to 3 g, 1.1 g to 3 g, 1 g to 3 g, 950 mg to 3 g, 900 mg to 3 g, 850 mg to 3 g, 800 mg to 3 g, 750 mg to 3 g, 700 mg to 3 g, 650 mg to 3 g, 600 mg to 3 g, 550 mg to 3 g, 500 mg to 3 g, 450 mg to 3 g, 400 mg to 3 g, 350 mg to 3 g, 300 mg to 3 g, 250 mg to 3 g, 200 mg to 3 g, 200 mg to 2 g, 250 mg to 2 g, 300 mg to 2 g, 350 mg to 2 g, 400 mg to 2 g, 450 mg to 2 g, 500 mg to 2 g, 550 mg to 2 g, 600 mg to 2 g, 650 mg to 2 g, 700 mg to 2 g, 750 mg to 2 g, 800 mg to 2 g, 850 mg to 2 g, 900 mg to 2 g, 950 mg to 2 g, 1 g to 2 g, 1.1 g to 2 g, 1.5 g to 2 g.

Non-limiting examples of dosage amount(s) of naltrexone in the presently disclosed implant include any dosage or amount in increments and/or combinations of 50 mg, 100 mg, 150 mg, 200 mg, 400 mg, 500 mg, 1 g, 1.1 g, 1.4 g, and the like. It will be appreciated that dosages or amounts incrementally between those described above are within the scope of the present disclosure.

The subcutaneous medical implant may comprise a single implant unit (or otherwise referred to as a pellet) configured to release a dosage amount of the naltrexone into a bloodstream of the patient. For example, for a subcutaneous biodegradable medical implant configured to release a dosage amount of 400 mg of naltrexone into a patient's bloodstream, a single 400 mg biodegradable naltrexone pellet may be used.

The subcutaneous medical implant may comprise a plurality of implant units configured to release a dosage amount of the naltrexone into a bloodstream of the patient. In some embodiments, the subcutaneous biodegradable medical implant comprises two or more implant units (or otherwise referred to as pellets). For example, for a subcutaneous biodegradable medical implant configured to release a dosage amount of 400 mg of naltrexone into a patient's bloodstream, two (2) 200 mg biodegradable naltrexone pellets may be used.

In one embodiment of the claimed invention, the implant may further comprise an outer sheath surrounding an inner core containing the naltrexone active agent. The outer sheath purpose is to separate the naltrexone core from the tissues of the human patient surrounding the implant once it is situated within the patient. Ideally, the outer sheath is inert. The sheath must be biodegradable allowing for the controlled, sustained, and/or gradual release of the naltrexone over an extended period of time. The outer sheath may partially coat the inner core, such as coating ninety percent or less of the inner core, eighty percent or less, seventy five percent or less, seventy percent or less, sixty five percent or less, sixty percent or less, fifty five percent or less or fifty percent or less. In a preferred embodiment, the outer sheath is cholesterol that is applied by dipping, spraying, brushing or spreading the cholesterol onto the outer surface of the naltrexone core. The release of the naltrexone over an extended period of time produces a local or systemic effect in the patient.

E. Shape, Number, and Insertion of Naltrexone Implants

In some embodiments, the subcutaneous biodegradable medical implants comprise one or more pellets formed of naltrexone and cholesterol in amounts described herein. In some embodiments, the present implants are tablet shaped, capsule shaped, rod-shaped, spherical, or cylindrical in shape. In some embodiments, the implants are approximately spherical in shape, wherein the diameter and height are approximately the same. In other embodiments, the implants are cylindrical are shaped like a rod. In other embodiments, the implants may further comprise a "belly-band." Regardless of the shape of the implants, they may have rounded edges, rounded ends, flat edges and/or flat ends.

Rate of release of naltrexone from the implant(s) into the patient's bloodstream is also varied by shape and number of pellets in a patient's treatment regimen. For example, an approximately spherical shaped pellet, with a smaller surface area than a rod-shaped pellet of the same volume, would release naltrexone more slowly than a rod-shaped pellet of the same volume. For example, implanting a single larger pellet would result in slower naltrexone release than multiple smaller pellets comprising the same total naltrexone dose as the single larger pellet.

Some treatment regimens utilize pellet shapes and sizes which are compatible with smaller patient incisions (e.g., incisions through which the pellets are subcutaneously placed within the patient body). Some patient incisions are closed with stitches or with 3M® Steri-Strips™ (3M® Company, St. Paul, MN). In some patients, smaller incisions and closure of incisions with Steri-Strips result in reduced pain for the patient from the procedure.

The subcutaneous biodegradable medical implant may be placed, injected, or inserted below a skin surface of the patient or may be placed or injected above a muscle fascia of the patient.

In embodiments of the present disclosure, an implant comprising naltrexone is placed, injected, or inserted beneath a surface of the skin in a lower abdominal area or hip area or other area of a patient. In some embodiments, the subcutaneous biodegradable medical implant is placed below a skin surface of a lower abdomen of the patient. In some embodiments, the subcutaneous biodegradable medical implant is placed below a skin surface of one or more of a hip, a leg, a back, and an arm of the patient. In some embodiments the implants disclosed herein are placed below a skin surface of a patient and above a muscle fascia of the patient. It will be appreciated that a placement location within a patient for a subcutaneous biodegradable medical implant is not limited to the examples herein and may vary according to a given indication or treatment plan.

F. Release into Bloodstream and Biodegradation of Pellets, Dosage Frequency

In embodiments, the subcutaneous biodegradable medical implant biodegrades in the patient. In some embodiments, the subcutaneous biodegradable medical implant biodegrades after a period of about 30 days in the patient. In embodiments, the subcutaneous biodegradable medical implant biodegrades over a period of about several months in the patient.

In an example, naltrexone is released from the implant into the bloodstream of a patient over a period of about 4 weeks to one year. In an example, naltrexone is released from the implant into the bloodstream of a patient over a period of about 4 weeks, 5 weeks, 6 weeks, 8 weeks, 9 weeks, 10 weeks, 11 weeks, 12 weeks, one month, 2 months, 3 months, 4 months, 5 months, 6 months, 7 months, 8 months, 9 months, 10 months, 11 months, 12 months, or one year. In an example, the implant biodegrades after a period of about 30 days, 4 weeks, 5 weeks, 6 weeks, 8 weeks, 9 weeks, 10 weeks, 11 weeks, 12 weeks, one month, 2 months, 3 months, 4 months, 5 months, 6 months, 7 months, 8 months, 9 months, 10 months, 11 months, 12 months, or one year in the patient. It will be appreciated that the time it takes to for an implant to biodegrade in a patient is dependent upon multiple factors including dosage, patient metabolism, external activity, and the like. In some embodiments, a second subcutaneous biodegradable medical implant is placed into a patient subsequent to a biodegradation time of a first subcutaneous biodegradable medical implant.

Exemplary timing of implants being inserted into a patient includes once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once a month, once every 2 months, once every 3 months, once every 4 months, once every 5 months, once every 6 months, once every 7 months, once every 8 months, once every 9 months, once every 10 months, once every 11 months, once every 12 months, once a year, or according to any other schedule determined by empirical analysis. Alternatively, insertions of naltrexone implants can be on an irregular basis as indicated by monitoring of symptoms of an addiction disorder, or by monitoring weight changes. It will be appreciated that, according to any given indication, a single insertion of a naltrexone implant described herein may be preferred (e.g., that is, replacement of the implant is not necessary to remain within the scope of the present disclosure).

G. Exemplary Placement of Naltrexone Implant in a Patient

In an example, the subcutaneous biodegradable medical implant is placed in a patient according to FIG. 10.

FIG. 10 is a diagram of an exemplary subcutaneous implant placed in a patient according to embodiments of the present disclosure. In embodiments of the present disclosure, a subcutaneous biodegradable medical implant comprising naltrexone 201 is placed into a patient 200. It will be appreciated that, while implant 201 is shown as having been placed into an abdominal area of patient 200, embodiments including placement of the implant into other areas of patient 200 are within the spirit of the present disclosure (e.g., lower abdominal area, hip area, as shown in FIG. 10. It will also be appreciated that implant 200 is not drawn to scale in FIG. 10. Preferably, the implant is implanted subcutaneously into the abdominal or pubic areas of the patient, more preferably, the lower abdominal. In yet another embodiment, the implant is implanted subcutaneously either above or below the patient's waistline and to the right or to the left of the patient's mid-line or directly above or below the belly button. In a further embodiment, the implant is implanted into the hip of the patient. In other embodiments, the implant is implanted subcutaneously into a patient so as to be orientated relatively parallel to the ground, wherein said implant orientation reduces mechanical irritation caused by the implant when the patient sits or bends forward.

A subcutaneous biodegradable medical implant may be inserted using an insertion device (e.g., a syringe, an applicator, a trocar, or any other appropriate insertion device).

H. Storage

The implants of the present invention may or may not be terminally sterilized before or after the implants are packaged transportation and long-term storage. If the pellets are sterilized, the preferred sterilization processes are gamma sterilization or e-beam sterilization. It is recommended that if gamma sterilization is selected that it be applied at a strength ranging from 25 eV to 40 eV±5%. The pellets, are typically stored in a sealed container, such as, but not limited to, a syringe, bottle, vial, blister pack or cartridge, which is typically suitable for long term storage, i.e., a "first storage means." "Suitable for long-term storage" means that the syringe, bottle, vial, blister pack or cartridge, does not allow for the escape of components of the pellets of the present invention or the ingress of external components, such as, microorganisms during long-term storage. After the pharmaceutical formulation is loaded into the first storage means, the first storage means may be sterilized and the sterilized first storage means may be stored in a second storage means, such as a pouch, vacuum-sealed wrapping, or any other storage means known in the art.

H. Conclusion

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A pharmaceutically-acceptable formulation consisting of (4R,4aS,7aR,12bS)-3-(cyclopropylmethyl)-4a,9-dihydroxy-2,4,5,6,7a,13-hexahydro-1H-4,12-methanobenzofuro[3,2-e]isoquinolin-7-one or salts thereof or anhydrous bases thereof or prodrugs thereof, and magnesium stearate, wherein the amount of (4R,4aS,7aR,12bS)-3-(cyclopropylmethyl)-4a,9-dihydroxy-2,4,5,6,7a,13-hexahydro-1H-4,12-methanobenzofuro[3,2-e]isoquinolin-7-one in the formulation is 1.5 grams±5% by weight; and the amount of magnesium stearate in the formulation is 0.011 grams by weight; and wherein the amount of magnesium stearate does not cause tissue irritation.

2. The pharmaceutically-acceptable formulation according to claim 1, wherein the pharmaceutically-acceptable formulation is terminally sterilized before or after packaging using gamma sterilization applied at a strength ranging from 25 eV to 40 eV±5%.

3. The formulation according to claim 1, wherein the formulation is in the form of a single pellet, a rod, a capsule or a tablet.

* * * * *